United States Patent
Grossman

(10) Patent No.: US 9,808,310 B2
(45) Date of Patent: *Nov. 7, 2017

(54) METHOD AND DEVICE FOR UTERINE FIBROID TREATMENT

(75) Inventor: Jessica Grossman, San Francisco, CA (US)

(73) Assignee: Gynesonics, Inc., Redwood City, CA (US)

( * ) Notice: Subject to any disclaimer, the term of this patent is extended or adjusted under 35 U.S.C. 154(b) by 275 days.

This patent is subject to a terminal disclaimer.

(21) Appl. No.: 12/973,642

(22) Filed: Dec. 20, 2010

(65) Prior Publication Data

US 2011/0087100 A1    Apr. 14, 2011

Related U.S. Application Data

(63) Continuation of application No. 11/347,018, filed on Feb. 2, 2006, now Pat. No. 7,918,795.

(60) Provisional application No. 60/710,712, filed on Aug. 22, 2005, provisional application No. 60/649,839, filed on Feb. 2, 2005.

(51) Int. Cl.
*A61B 8/00* (2006.01)
*A61B 18/14* (2006.01)
*A61B 18/00* (2006.01)
*A61B 90/00* (2016.01)

(52) U.S. Cl.
CPC ............ *A61B 18/1477* (2013.01); *A61B 2018/00559* (2013.01); *A61B 2018/143* (2013.01); *A61B 2090/378* (2016.02); *A61B 2090/3782* (2016.02)

(58) Field of Classification Search
CPC .... A61B 2018/00559; A61B 2018/143; A61B 2090/378; A61B 2090/3782
USPC ........ 600/439, 437, 462, 459, 210; 601/1-4; 606/170, 180, 45.1, 13-15, 40, 42, 41; 604/113, 105
See application file for complete search history.

(56) References Cited

U.S. PATENT DOCUMENTS

| | | | |
|---|---|---|---|
| 4,869,258 A * | 9/1989 | Hetz | 600/446 |
| 4,936,281 A | 6/1990 | Stasz | |
| 5,090,414 A * | 2/1992 | Takano | 600/461 |

(Continued)

FOREIGN PATENT DOCUMENTS

| WO | WO 97/17105 A1 | 5/1997 |
|---|---|---|
| WO | WO 98/11834 A1 | 3/1998 |

(Continued)

OTHER PUBLICATIONS

Notice of allowance dated Oct. 5, 2010 for U.S. Appl. No. 11/347,018.

(Continued)

*Primary Examiner* — Long V Le
*Assistant Examiner* — Katherine McDonald
(74) *Attorney, Agent, or Firm* — Wilson, Sonsini, Goodrich & Rosati

(57) ABSTRACT

Methods and devices for both imaging and treating uterine fibroid tumors in one real-time system are provided. One minimally invasive method comprises introducing a sheath into a uterus and determining a location of a fibroid using a visualization element within or on the sheath. Upon identification, a portion of the sheath is steered to position at least one treatment needle at the determined location. The needle is then anchored in uterine tissue and the fibroid treated with the needle.

11 Claims, 26 Drawing Sheets

(56) References Cited

U.S. PATENT DOCUMENTS

| | | | |
|---|---|---|---|
| 5,372,587 A | 12/1994 | Hammerslag et al. | |
| 5,456,689 A | 10/1995 | Kresch | |
| 5,469,853 A * | 11/1995 | Law et al. | 600/463 |
| 5,471,988 A | 12/1995 | Fujio et al. | |
| 5,474,075 A * | 12/1995 | Goldberg et al. | 600/463 |
| 5,492,126 A | 2/1996 | Hennige et al. | |
| 5,527,331 A | 6/1996 | Kresch et al. | |
| 5,662,664 A | 9/1997 | Gordon et al. | |
| 5,666,954 A | 9/1997 | Chapelon et al. | |
| 5,697,897 A | 12/1997 | Buchholtz et al. | |
| 5,730,752 A | 3/1998 | Alden et al. | |
| 5,741,287 A | 4/1998 | Alden et al. | |
| 5,769,880 A | 6/1998 | Truckai et al. | |
| 5,860,974 A | 1/1999 | Abele | |
| 5,863,294 A | 1/1999 | Alden | |
| 5,873,828 A | 2/1999 | Fujio et al. | |
| 5,876,340 A | 3/1999 | Tu et al. | |
| 5,876,399 A | 3/1999 | Chia et al. | |
| 5,891,137 A | 4/1999 | Chia et al. | |
| 5,906,615 A | 5/1999 | Thompson | |
| 5,916,198 A | 6/1999 | Dillow | |
| 5,957,941 A | 9/1999 | Ream | |
| 5,979,452 A | 11/1999 | Fogarty et al. | |
| 5,979,453 A | 11/1999 | Savage et al. | |
| 5,984,942 A | 11/1999 | Alden et al. | |
| 6,002,968 A | 12/1999 | Edwards | |
| 6,007,499 A | 12/1999 | Martin et al. | |
| 6,032,673 A | 3/2000 | Savage et al. | |
| 6,039,748 A | 3/2000 | Savage et al. | |
| 6,059,766 A | 5/2000 | Greff | |
| 6,077,257 A | 6/2000 | Edwards et al. | |
| 6,141,577 A | 10/2000 | Rolland et al. | |
| 6,146,378 A | 11/2000 | Mikus et al. | |
| 6,158,250 A | 12/2000 | Tibbals, Jr. et al. | |
| 6,190,383 B1 | 2/2001 | Schmaltz et al. | |
| 6,193,714 B1 | 2/2001 | McGaffigan et al. | |
| 6,211,153 B1 | 4/2001 | Gamick et al. | |
| 6,254,601 B1 | 7/2001 | Burbank et al. | |
| 6,280,441 B1 | 8/2001 | Ryan | |
| 6,296,639 B1 | 10/2001 | Truckai et al. | |
| 6,306,129 B1 | 10/2001 | Lithe et al. | |
| 6,315,741 B1 | 11/2001 | Martin et al. | |
| 6,379,348 B1 | 4/2002 | Onik | |
| 6,405,732 B1 | 6/2002 | Edwards et al. | |
| 6,419,648 B1 | 7/2002 | Vitek et al. | |
| 6,419,653 B2 | 7/2002 | Edwards et al. | |
| 6,419,673 B1 | 7/2002 | Edwards et al. | |
| 6,425,867 B1 | 7/2002 | Vaezy et al. | |
| 6,432,067 B1 | 8/2002 | Martin et al. | |
| 6,461,296 B1 | 10/2002 | Desai | |
| 6,463,331 B1 | 10/2002 | Edwards | |
| 6,468,228 B1 * | 10/2002 | Topel et al. | 600/567 |
| 6,482,203 B2 | 11/2002 | Paddock et al. | |
| 6,485,413 B1 | 11/2002 | Boppart et al. | |
| 6,506,154 B1 | 1/2003 | Ezion et al. | |
| 6,506,156 B1 | 1/2003 | Jones et al. | |
| 6,506,171 B1 | 1/2003 | Vitek et al. | |
| 6,507,747 B1 | 1/2003 | Gowda et al. | |
| 6,508,815 B1 | 1/2003 | Strul et al. | |
| 6,522,142 B1 | 2/2003 | Freundlich | |
| 6,540,677 B1 | 4/2003 | Angelsen et al. | |
| 6,543,272 B1 | 4/2003 | Vitek | |
| 6,550,482 B1 | 4/2003 | Burbank et al. | |
| 6,554,780 B1 | 4/2003 | Sampson et al. | |
| 6,559,644 B2 | 5/2003 | Froundlich et al. | |
| 6,569,159 B1 | 5/2003 | Edwards et al. | |
| 6,589,237 B2 | 7/2003 | Woloszko et al. | |
| 6,602,251 B2 | 8/2003 | Burbank et al. | |
| 6,610,054 B1 | 8/2003 | Edwards et al. | |
| 6,612,988 B2 | 9/2003 | Maor et al. | |
| 6,613,004 B1 | 9/2003 | Vitek et al. | |
| 6,613,005 B1 | 9/2003 | Friedman et al. | |
| 6,623,481 B1 | 9/2003 | Garbagnati et al. | |
| 6,626,854 B2 | 9/2003 | Friedman et al. | |
| 6,626,855 B1 | 9/2003 | Weng et al. | |
| 6,632,193 B1 | 10/2003 | Davison et al. | |
| 6,635,055 B1 | 10/2003 | Cronin | |
| 6,635,065 B2 | 10/2003 | Burbank et al. | |
| 6,638,275 B1 | 10/2003 | McGaffigan | |
| 6,638,286 B1 | 10/2003 | Burbank et al. | |
| 6,645,162 B2 | 11/2003 | Friedman et al. | |
| 6,652,516 B1 | 11/2003 | Gough | |
| 6,654,202 B2 | 11/2003 | Pless et al. | |
| 6,660,002 B1 | 12/2003 | Edwards et al. | |
| 6,660,024 B1 * | 12/2003 | Flaherty | A61B 17/3403 600/439 |
| 6,663,624 B2 | 12/2003 | Edwards et al. | |
| 6,663,626 B2 | 12/2003 | Truckai et al. | |
| 6,666,833 B1 | 12/2003 | Friedman et al. | |
| 6,679,855 B2 | 1/2004 | Horn et al. | |
| 6,685,639 B1 | 2/2004 | Wang et al. | |
| 6,689,128 B2 | 2/2004 | Sliwa, Jr. et al. | |
| 6,692,490 B1 | 2/2004 | Edwards | |
| 6,701,931 B2 | 3/2004 | Sliwa, Jr. et al. | |
| 6,705,994 B2 | 3/2004 | Vortman et al. | |
| 6,712,815 B2 | 3/2004 | Sampson et al. | |
| 6,716,184 B2 | 4/2004 | Vaezy et al. | |
| 6,719,755 B2 | 4/2004 | Sliwa, Jr. et al. | |
| 6,728,571 B1 | 4/2004 | Barbato | |
| 6,730,081 B1 | 5/2004 | Desai | |
| 6,735,461 B2 | 5/2004 | Vitek et al. | |
| 6,743,184 B2 | 6/2004 | Sampson et al. | |
| 6,746,447 B2 | 6/2004 | Davison et al. | |
| 6,764,488 B1 | 7/2004 | Burbank et al. | |
| 6,773,431 B2 | 8/2004 | Eggers et al. | |
| 6,790,180 B2 | 9/2004 | Vitek | |
| 6,805,128 B1 | 10/2004 | Pless et al. | |
| 6,805,129 B1 | 10/2004 | Pless et al. | |
| 6,813,520 B2 | 11/2004 | Truckai et al. | |
| 6,832,996 B2 | 12/2004 | Woloszko et al. | |
| 6,837,887 B2 | 1/2005 | Woloszko et al. | |
| 6,837,888 B2 | 1/2005 | Ciarrocca et al. | |
| 6,840,935 B2 | 1/2005 | Lee | |
| 6,936,048 B2 | 8/2005 | Hurst | |
| 6,944,490 B1 | 9/2005 | Chow | |
| 6,969,354 B1 | 11/2005 | Marian | |
| 7,160,296 B2 | 1/2007 | Pearson et al. | |
| 7,229,401 B2 | 6/2007 | Kindlein | |
| 7,247,141 B2 | 7/2007 | Makin et al. | |
| 7,387,628 B1 | 6/2008 | Behl et al. | |
| 7,517,346 B2 | 4/2009 | Sloan et al. | |
| 7,918,795 B2 | 4/2011 | Grossman | |
| 7,963,941 B2 | 6/2011 | Wilk | |
| 8,080,009 B2 | 12/2011 | Lee et al. | |
| 8,157,741 B2 | 4/2012 | Hirota | |
| 8,157,745 B2 | 4/2012 | Schoot | |
| 8,216,231 B2 | 7/2012 | Behl et al. | |
| 8,221,321 B2 | 7/2012 | McMorrow et al. | |
| 8,287,485 B2 | 10/2012 | Kimura et al. | |
| 8,377,041 B2 | 2/2013 | Frassica et al. | |
| 8,469,893 B2 | 6/2013 | Chiang et al. | |
| 8,512,330 B2 | 8/2013 | Epstein et al. | |
| 8,512,333 B2 | 8/2013 | Epstein et al. | |
| 8,540,634 B2 | 9/2013 | Bruce et al. | |
| 8,585,598 B2 | 11/2013 | Razzaque et al. | |
| 8,622,911 B2 | 1/2014 | Hossack et al. | |
| 8,663,130 B2 | 3/2014 | Neubach et al. | |
| 8,718,339 B2 | 5/2014 | Tonomura et al. | |
| 8,814,796 B2 | 8/2014 | Martin et al. | |
| 9,089,287 B2 | 7/2015 | Sliwa et al. | |
| 9,198,707 B2 | 12/2015 | McKay et al. | |
| 9,198,719 B2 | 12/2015 | Murdeshwar et al. | |
| 9,247,925 B2 | 2/2016 | Havel et al. | |
| 9,439,627 B2 | 9/2016 | Case et al. | |
| 9,510,898 B2 | 12/2016 | Epstein et al. | |
| 9,516,996 B2 | 12/2016 | Diolaiti et al. | |
| 2001/0014805 A1 | 8/2001 | Burbank et al. | |
| 2001/0051802 A1 | 12/2001 | Woloszko et al. | |
| 2002/0022835 A1 | 2/2002 | Lee | |
| 2002/0052600 A1 | 5/2002 | Davison et al. | |
| 2002/0068871 A1 | 6/2002 | Mendlein et al. | |
| 2002/0077550 A1 | 6/2002 | Rabiner et al. | |
| 2002/0183735 A1 * | 12/2002 | Edwards et al. | 606/32 |
| 2003/0009164 A1 | 1/2003 | Woloszko et al. | |

(56) References Cited

U.S. PATENT DOCUMENTS

| | | |
|---|---|---|
| 2003/0014046 A1 | 1/2003 | Edwards |
| 2003/0028111 A1 | 2/2003 | Vaezy et al. |
| 2003/0130575 A1 | 7/2003 | Desai et al. |
| 2003/0130655 A1 | 7/2003 | Woloszko et al. |
| 2003/0195420 A1 | 10/2003 | Mendlein et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0030268 A1 | 2/2004 | Weng et al. |
| 2004/0054366 A1 | 3/2004 | Davison et al. |
| 2004/0082883 A1* | 4/2004 | Kohno ............................. 601/2 |
| 2004/0120668 A1 | 6/2004 | Loeb |
| 2004/0143252 A1 | 7/2004 | Hurst |
| 2004/0153057 A1 | 8/2004 | Davison |
| 2004/0175399 A1 | 9/2004 | Schiffman |
| 2004/0176760 A1 | 9/2004 | Qiu |
| 2004/0193028 A1 | 9/2004 | Jones et al. |
| 2004/0199179 A1* | 10/2004 | Elliott ........................... 606/128 |
| 2004/0215182 A1 | 10/2004 | Lee |
| 2004/0230190 A1 | 11/2004 | Dahla et al. |
| 2004/0254572 A1 | 12/2004 | McIntyre et al. |
| 2005/0038340 A1 | 2/2005 | Vaezy et al. |
| 2005/0085730 A1* | 4/2005 | Flesch et al. ................. 600/459 |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0197577 A1 | 9/2005 | Makin et al. |
| 2005/0215990 A1 | 9/2005 | Govan |
| 2005/0228288 A1 | 10/2005 | Hurst |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0178665 A1 | 8/2006 | Sloan |
| 2006/0184049 A1 | 8/2006 | Tsujita |
| 2007/0006215 A1 | 1/2007 | Epstein et al. |
| 2007/0179380 A1 | 8/2007 | Grossman |
| 2008/0228081 A1 | 9/2008 | Becker et al. |
| 2009/0043295 A1 | 2/2009 | Arnal et al. |
| 2010/0262133 A1 | 10/2010 | Hoey et al. |
| 2012/0165813 A1 | 6/2012 | Lee et al. |
| 2012/0209115 A1 | 8/2012 | Tonomura |
| 2012/0277737 A1 | 11/2012 | Curley |
| 2013/0281863 A1 | 10/2013 | Chiang et al. |
| 2013/0317513 A1 | 11/2013 | Hirayama et al. |
| 2014/0180273 A1 | 6/2014 | Nair |
| 2014/0276081 A1 | 9/2014 | Tegels |
| 2015/0150497 A1 | 6/2015 | Goldchmit |
| 2015/0173592 A1 | 6/2015 | Leeflang et al. |
| 2015/0257779 A1 | 9/2015 | Sinelnikov et al. |
| 2016/0151041 A1 | 6/2016 | Lee et al. |
| 2016/0278740 A1 | 9/2016 | Negrila et al. |
| 2016/0310042 A1 | 10/2016 | Kesten et al. |

FOREIGN PATENT DOCUMENTS

| | | |
|---|---|---|
| WO | WO 98/14169 A1 | 4/1998 |
| WO | WO 99/43366 A1 | 9/1999 |
| WO | WO 00/00098 A1 | 1/2000 |
| WO | WO 01/80723 A2 | 11/2001 |
| WO | WO 01/95819 A1 | 12/2001 |
| WO | WO 02/11639 A1 | 2/2002 |
| WO | WO 01/80723 A3 | 4/2002 |
| WO | WO 03/005882 A2 | 1/2003 |
| WO | WO 03/065908 A1 | 8/2003 |
| WO | WO 03/005882 A3 | 11/2003 |
| WO | WO 2004/002293 A2 | 1/2004 |
| WO | WO 2004/002550 A2 | 1/2004 |
| WO | WO 2004/020011 A1 | 3/2004 |
| WO | WO 2004/035110 A2 | 4/2004 |
| WO | WO 2004/035110 A3 | 6/2004 |
| WO | WO 2004/058328 A2 | 7/2004 |
| WO | WO 2004/064658 A1 | 8/2004 |
| WO | WO 2004/002550 A3 | 10/2004 |
| WO | WO 2004/058328 A3 | 10/2004 |
| WO | WO 2004/002293 A3 | 7/2005 |
| WO | WO-2007149595 A2 | 12/2007 |

OTHER PUBLICATIONS

Office action dated Jan. 23, 2009 for U.S. Appl. No. 11/347,018.
Office action dated Sep. 17, 2009 for U.S. Appl. No. 11/347,018.
Office action dated Dec. 22, 2009 for U.S. Appl. No. 11/347,018.
Bergamini, et al. Laparoscopic Radiofrequency Thermal Ablation: A New Approach to Symptomatic Uterine Myomas. Am. J. Obstetrics and Gynecology (2005) 192: 768-73.
CNN.com Health Women. Experimental technique uses lasers to shrink uterine fibroids. Nov. 28, 2000.
Hindley, et al. MRI guidance of focused ultrasound therapy of uterine fibroids: Early results. American Journal of Roentgenology, 2004, 183(6): 1173-1719.
Kanaoka, et al. Microwave endometrial ablation at a frequency of 2.45 Ghz. A pilot study. J Reprod Med. Jun. 2001; 46(60): 559-63.
Law, et al. Magnetic resonance-guided percutaneous laser ablation of uterine fibroids. J Magn Reson Imaging, Oct. 2000; 12(4):565-70.
Liu, et al. Catheter-Based Intraluminal Sonography. J. Ultrasound Med., 2004, 23:145-160.
Mogami, et al. Usefulness of MR-guided percutaneous cryotherapy. Med. Imaging Technol. 2004, 22(3): 131-6. (English abstract).
MSNBC OnLine Articles, About Us: Articles; "Intrauerine Fibroids Can Now Be Treated Nonsurgically".
RSNA 2000 Explore News Release. Lasers Liquefy Uterine Fibroid Tumors. 11:30 a.m. CST, Monday, Nov. 27, 2000.
Senoh, et al. Saline Infusion Contrast Intrauterine Sonographic Assessment of the Endometrium with High-Frequency, Real-Time Miniature Transducer Normal Menstrual Cycle: a Preliminary Report. Human Reproduction, 14 (10): 2600-2603, 1999.
Vascular and Interventional Radiology, SRSC; Nonsurgical Treatment of Uterine Fibroids.
Websand, Inc., New treatment options for fibroid tumors, Copyright 2002 by WebSand, Inc.
U.S. Appl. No. 60/758,881, filed Jan. 12, 2006.

\* cited by examiner

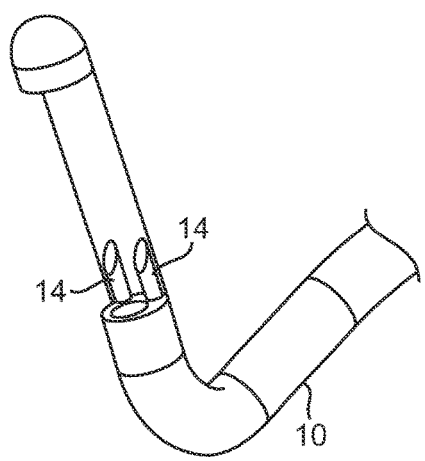
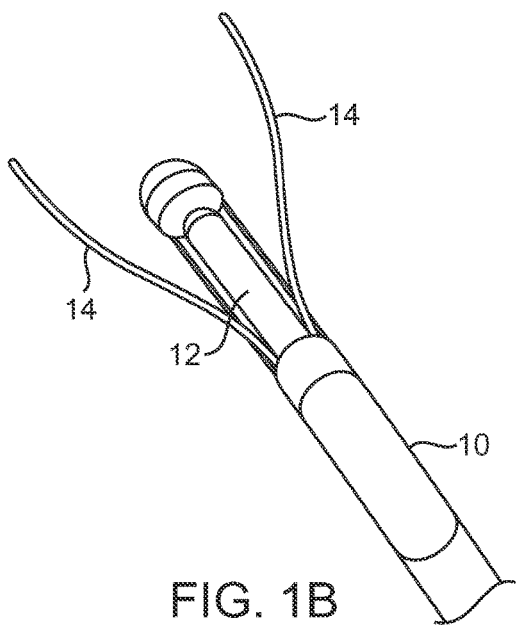
FIG. 1A    FIG. 1B
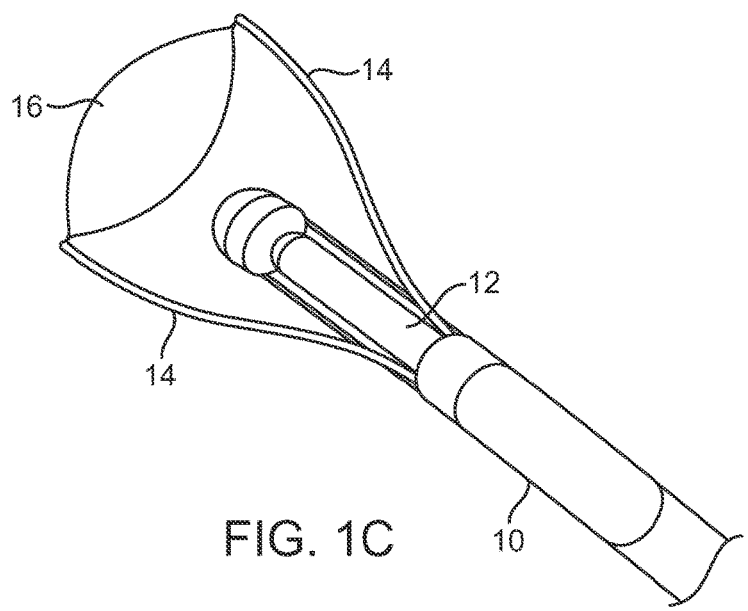
FIG. 1C

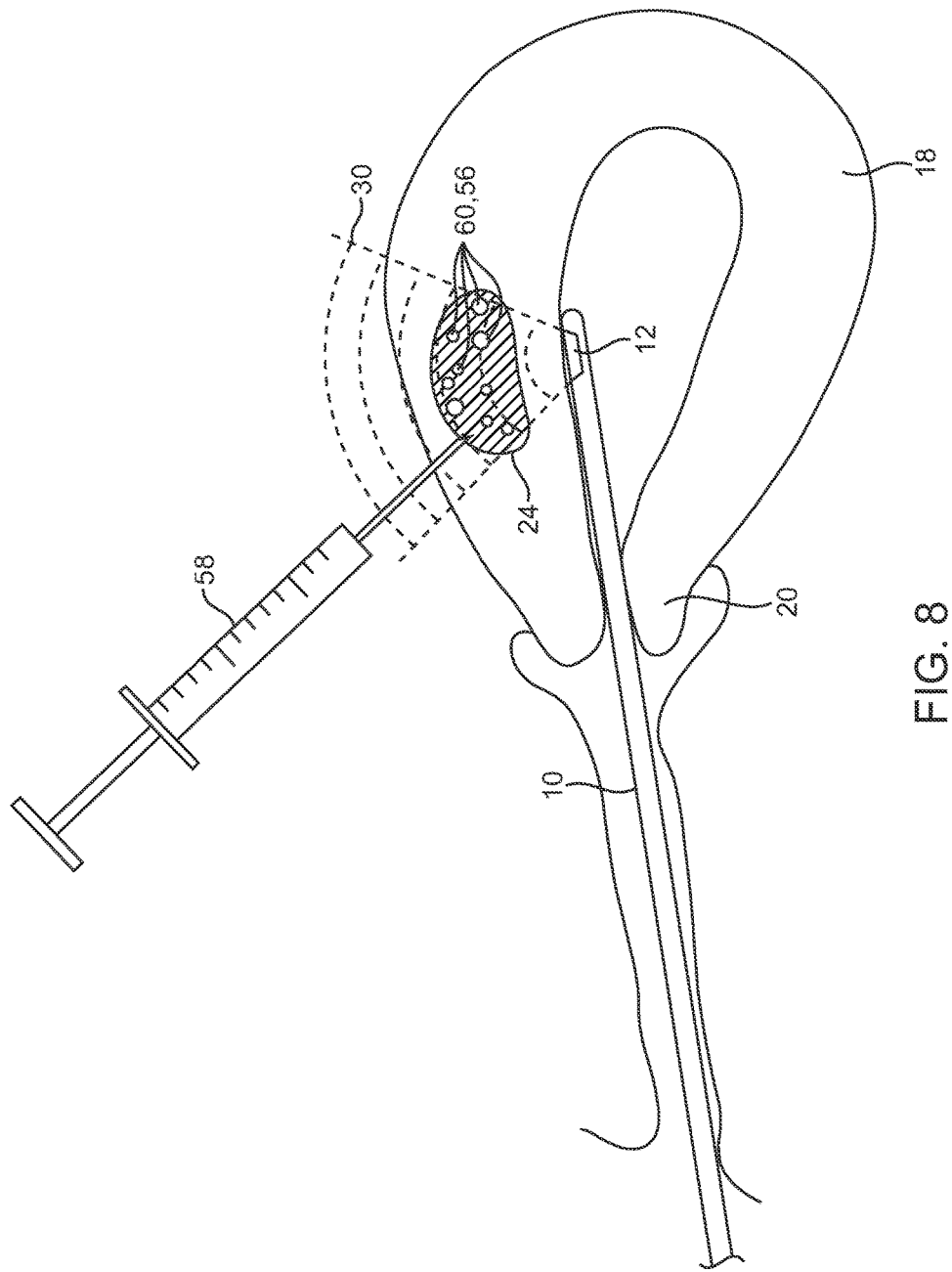

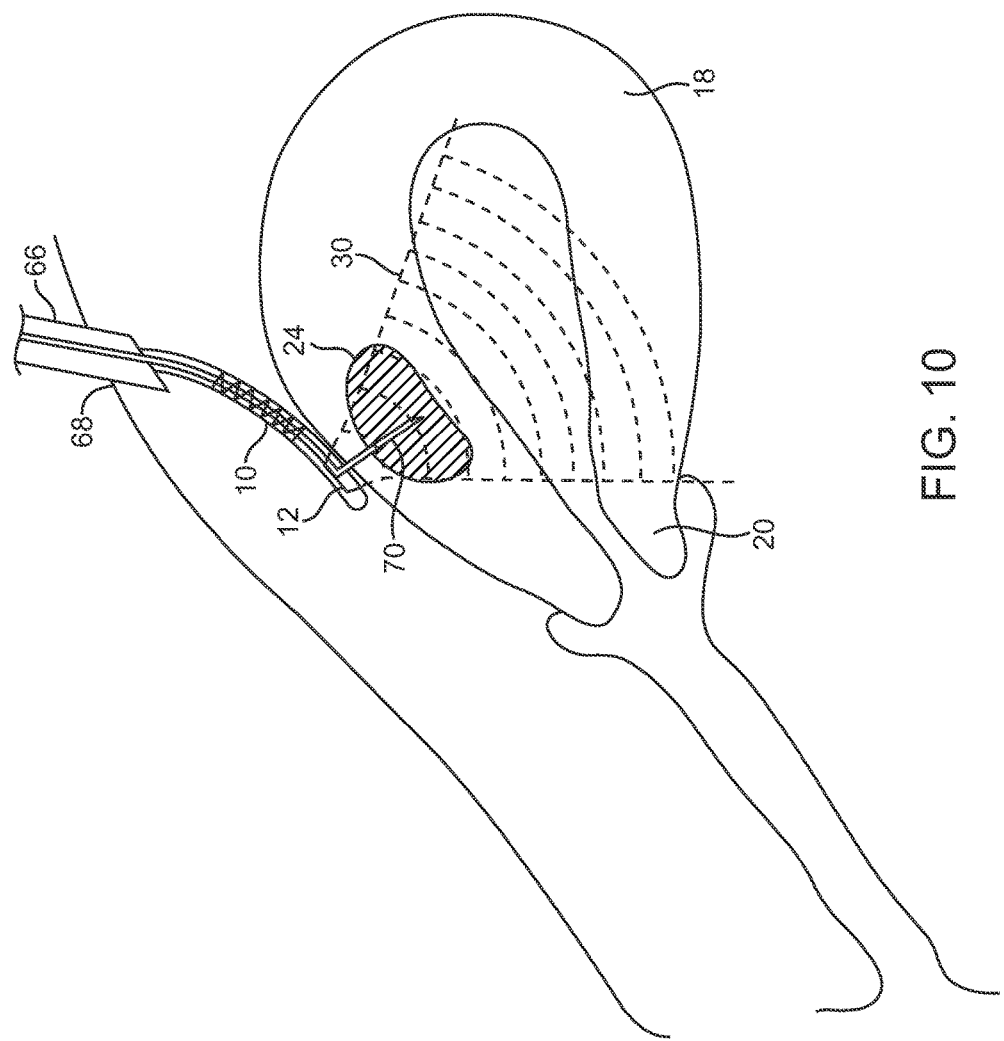

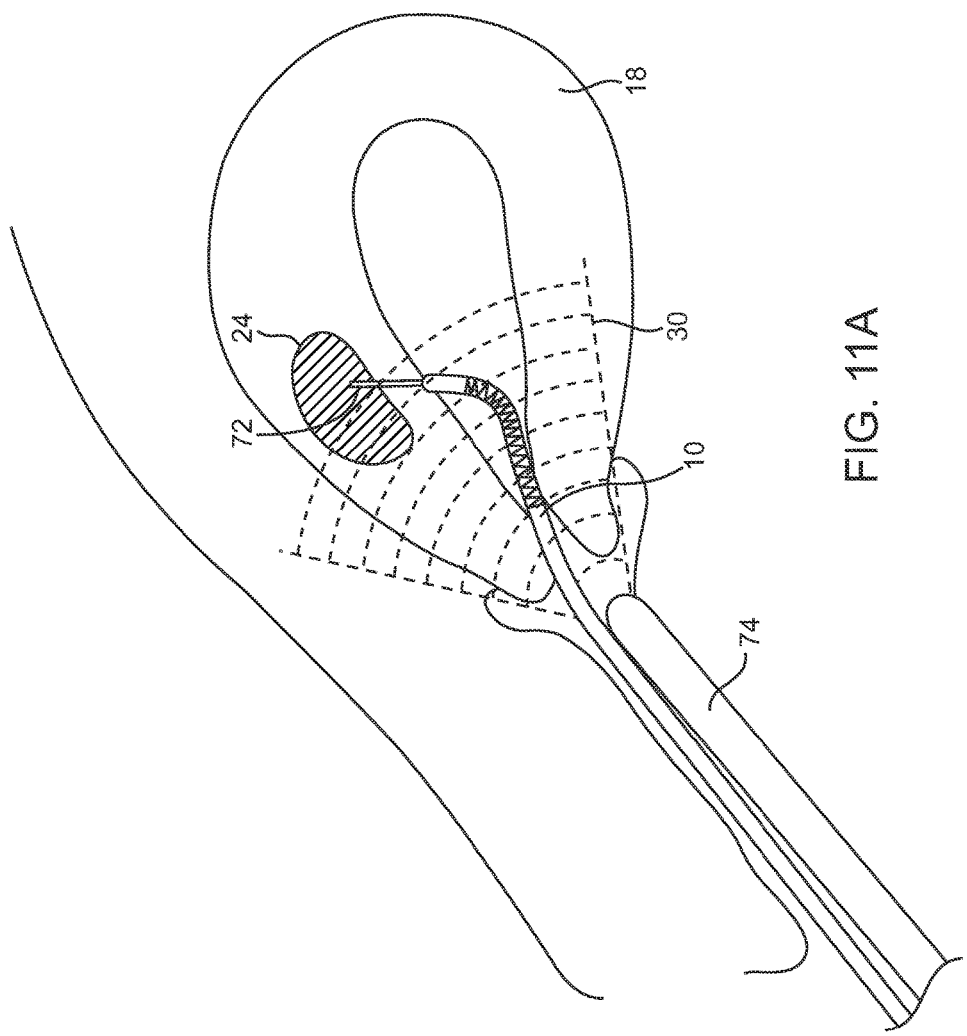

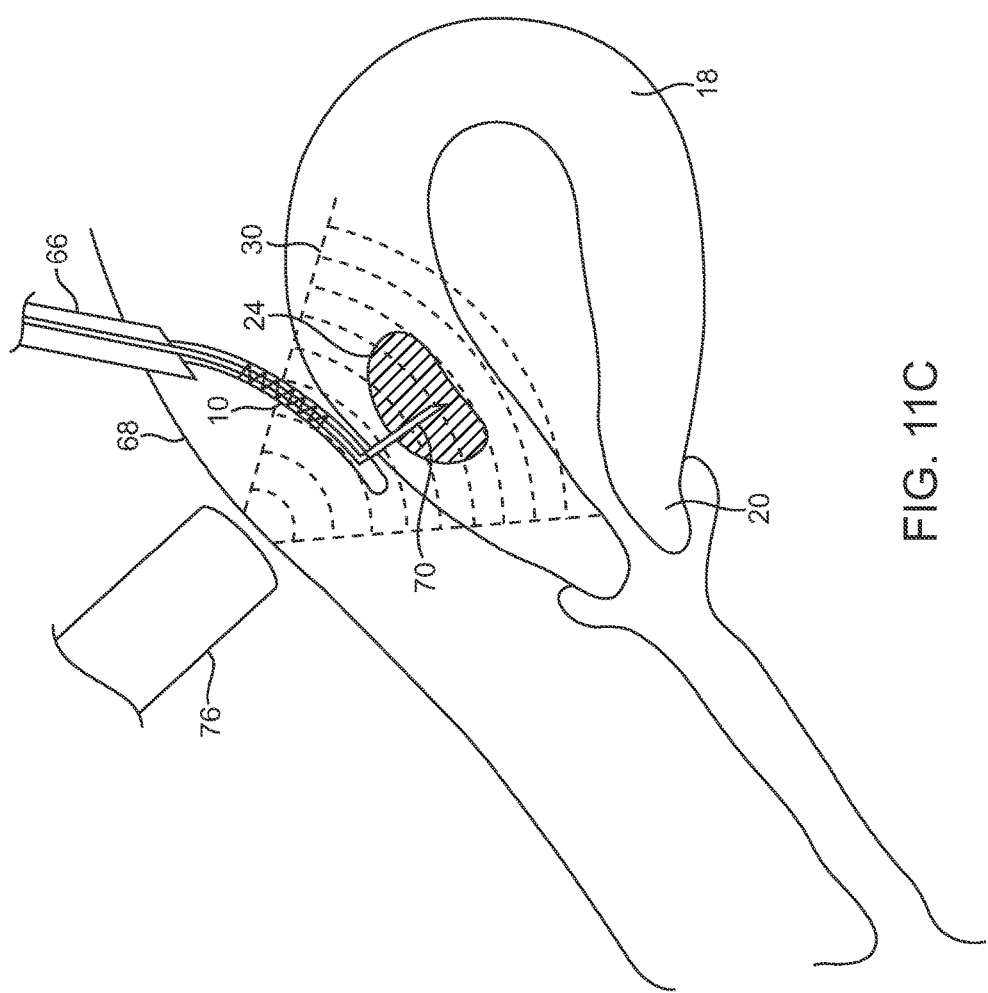

METHOD AND DEVICE FOR UTERINE FIBROID TREATMENT

CROSS-REFERENCES TO RELATED APPLICATIONS

The present application is a continuation of U.S. patent application Ser. No. 11/347,018 filed Feb. 2, 2006, which claims the benefit of Provisional Patent Application Nos. 60/710,712, filed Aug. 22, 2005, and 60/649,839, filed Feb. 2, 2005, the full disclosures of which are incorporated herein by reference.

BACKGROUND OF THE INVENTION

Field of the Invention

The present invention relates generally to medical devices and methods. More particularly, the invention relates to methods and devices for locating and treating uterine fibroids.

There are unmet needs in the pathophysiology of the female reproductive tract, such as dysfunctional uterine bleeding and fibroids. Fibroids are benign tumors of the uterine myometria (i.e., muscle) and are the most common tumor of the female pelvis. Fibroid tumors affect up to 30% of women of childbearing age and can cause significant symptoms such as discomfort, pelvic pain, mennorhagia, pressure, anemia, compression, infertility and miscarriage. Fibroids may be located in the myometrium (i.e., intramural), adjacent to the endometrium (i.e., submucosal), or in the outer layer of the uterus (i.e., subserosal). Most commonly fibroids are a smooth muscle overgrowth that arise intramurally and can grow to be several centimeters in diameter.

Current treatment for fibroids includes medical treatment with NSAIDS, estrogen-progesterone combinations, and GnRH analogues. Pharmacologic therapy with GnRH analogues is limited due to its side effects, such as hot flashes, vaginal dryness, mood changes and bone density loss. Further, its relatively short time of treatment (e.g., 3 months) offers temporary shrinkage, wherein the fibroids usually regrow after medical discontinuation. Pharmacologic therapy is relatively ineffective and palliative rather than curative.

Hysterectomy (i.e., surgical removal of the uterus) is a common treatment for fibroids. It is performed up to 600,000 times annually in the United States. Indeed, fibroids are the indication for hysterectomy in up to one third of all cases. Hysterectomy for treating fibroids may be very effective but has many undesirable side effects such as loss of fertility, open surgery, sexual dysfunction, and long recovery time. There is also significant morbidity (e.g., sepsis, hemorrhage, peritonitis, bowel and bladder injury), mortality, and costs associated with hysterectomy treatments.

Surgical myomectomy is also an open surgical procedure requiring laparotomy and general anesthesia in which fibroids are removed. Often these procedures result in significant blood loss and can only remove a portion of the culprit tissue. In the early 1990's there was a growth in advanced operative laparoscopy techniques and laparoscopic myomectomy was pioneered. However, laparoscopic myomectomy remains technically challenging. For example, it requires laparoscopic suturing which is performed only by the most skilled of laparoscopic gynecologists. Further, prolonged anesthesia time, increased blood loss, and possibly higher risk of uterine rupture in pregnancy make laparoscopic myomectomy a challenging procedure. Currently, the removal of subserosal or intramural fibroids requires an abdominal approach.

Hysteroscopy (i.e., process by which a thin fiber optic camera is used to image inside the uterus) may include an attachment to destroy tissue. Hysteroscopic resection is a surgical technique that uses a variety of devices (e.g., loops, roller balls, bipolar electrodes) to ablate or resect uterine tissue. The uterus needs to be filled with fluid for better viewing and thus has potential side effects of fluid overload. Hysteroscopic ablation is also limited by its visualization technique and is thus only appropriate for those fibroids that are submucosal and/or protrude into the uterine cavity.

Uterine artery embolization has also been suggested as an alternative minimally invasive treatment for fibroids. Uterine artery embolization was introduced in the early 1990's and is performed by injecting small particles through a groin incision into the uterine artery to selectively block the blood supply to fibroids. Uterine artery embolization results in reduction of the myoma size from 20-70% at six months. However, side effects of this procedure include pelvic infection, premature menopause, and severe pelvic pain. In addition, long term MRI data suggest that incomplete fibroid infarction may result in regrowth of infracted fibroid tissue. Despite much interest in uterine artery embolization, the procedure rates remain low and have not grown past a few thousand performed per year in the United States. This may be due to the fact that interventional radiologists, instead of gynecologists who know how to diagnose and treat fibroid tumors, are the ones who perform uterine artery embolization procedures.

Endometrial ablation, which is primarily a procedure for dysfunctional or abnormal uterine bleeding, may be used at times for fibroids. Recently there have been many new technologies to perform endometrial ablation such as cryo energy, microwave energy, and impedance controlled radiofrequency. Endometrial ablation destroys the endometrial tissue lining the uterus, but does not specifically treat fibroids. This technique is also not suitable for women who desire to bear children. Endometrial ablation remains a successful therapy for dysfunctional uterine bleeding, but is limited in its ability to treat fibroids.

Myolysis is another alternative minimally invasive technique for fibroid treatment. Myolysis was first performed in the 1980's in Europe by using lasers to coagulate tissue, denature proteins, and necrose myometrium with laparoscopic visualization. This technique has been in use for the past several years and involves applying energy directly to the myoma. Laparoscopic myolysis can be an alternative to myomectomy, as the fibroids are coagulated and then undergo coagulative necrosis resulting in a dramatic decrease in size. Shrinkage of fibroids has been reported at 30-50%. In addition there is the obvious economic benefit of out-patient surgery, rapid recovery, and return to normal lifestyle. However, all laparoscopic techniques are limited by the fact that they can only see, and therefore only treat, subserosal fibroids.

Needle myolysis is a promising technique whereby a laparoscope is used to introduce one or more needles into a fibroid tumor under visual control. Bipolar radiofrequency current is then delivered between two adjacent needles, or monopolar current between a single needle and a distant dispersive electrode affixed to the thigh or back. The aim of needle myolysis is to coagulate a significant volume of the tumor and thereby cause it to shrink substantially. The traditional technique is to make multiple passes through different areas of the tumor using the coagulating needle to destroy many cylindrical cores of abnormal tissue. However, the desirability of multiple passes is mitigated by the risk of adhesion formation, which is thought to increase with increasing amounts of injured uterine serosa and by the operative time and skill required.

For these and other reasons, it would be desirable to provide a minimally invasive method and device to selectively eradicate fibroid tumors within the uterus. It would be desirable if the method and device could locate and treat all types of fibroids in the uterus in a safe and effective manner with minimum risk and discomfort for the patient. It would be further desirable to provide a method and device for eradicating fibroid tumors that combines imaging and treatment in one simple hand held device. At least some of these objectives will be met by the methods and devices of the present invention described hereinafter.

Description of the Background Art

Relevant references include U.S. Pat. No. 5,456,689 Kresch et al.; U.S. Pat. No. 5,979,453 Savage et al.; U.S. Pat. No. 6,002,968 Edwards; U.S. Pat. No. 6,550,482 Burbank et al.; U.S. Pat. No. 6,626,855 Weng et al.; U.S. Pat. No. 6,716,184 Vaezy et al.; WO 2004/064658; and US 2005/0107781. The full disclosures of each of the above references are incorporated herein by reference.

BRIEF SUMMARY OF THE INVENTION

In a first aspect of the present invention, methods for minimally invasive identification and treatment of submucosal, intramural, or subserosal fibroids of the uterus are provided. A sheath, catheter, or probe may be transcervically introduced into the uterus. A location of the fibroid tumor may be determined by using a visualization element within or on the sheath. Preferably, the physician will be able to image the tumors transendometrially from within the uterine cavity. The visualization element may comprise an ultrasonic element or other visualization means, such as hysteroscopy, that is capable of producing a visual image. Once having identified the location, a portion of the sheath is steered to position at least one treatment needle at the determined location. The needle is anchored within the uterine tissue and the fibroid is treated with the needle. Fibroid treatment may take several forms as discussed in more detail below. Generally, each individual fibroid tumor will be navigated to, imaged, targeted and treated separately. It will further be appreciated that external imaging may be preformed prior to sheath introduction so as to initially "map" the location of the fibroid tumors.

Anchoring comprises manually positioning and penetrating the treatment needle through an endometrium so as to engage the fibroid. Preferably, the visualization element not only provides a field of view for locating the fibroid but also provides a field of view for directly observing and verifying needle deployment and fibroid treatment in real-time. Visualization may be aided by steering, rotating, or deflecting the visualization element independent of the treatment needle so as to provide a complete view. At least one treatment needle, preferably two treatment needles, will be anchored in the uterine tissue so that the needles will remain substantially immobile during the delivery of treatment. For example, anchoring may comprise deploying at least two treatment needles in a converging manner so as to pinch the fibroid therebetween. Alternatively, anchoring may comprise deploying at least two treatment needles in a diverging manner so as to hook the fibroid therebetween. Still further, anchoring may comprise deploying at least two treatment needles in a telescoping manner.

The uterine fibroid may be treated in several ways. Usually the fibroid will be treated by delivering ablative energy to the fibroid with the needle to necrose the tissue. The ablative energy may comprise electrically energy (e.g., radiofrequency energy, laser energy, or microwave energy), freezing energy (e.g., cryo energy), ultrasound energy, high intensity focused ultrasound (HIFU), or radiation. Preferably, the treatment needle comprises electrically conductive electrodes that deliver ablative radiofrequency energy in a bipolar or monopolar fashion. In addition to or in lieu of ablative energy treatment, the fibroids may be treated by delivering at least one therapeutic agent to the fibroid with the needle. Still further, and in addition to or in lieu of energy and/or drug delivery treatments, the fibroid may be treated by mechanical cutting. For example, the fibroid may be morcelated with a tip of the needle. The treatment needle or other elements (e.g., non-treatment needle, thermocouple) may additionally monitor tissue impedance and/or measure a tissue temperature so as to aid in diagnosis, blood supply measurement, thermal signature, tissue targeting, and the like.

In another aspect of the present invention, minimally invasive devices for imaging and treating submucosal, intramural, or subserosal fibroids in one real-time system are provided. The device comprises a sheath, probe, catheter, or other shaft which is adapted for transcervical introduction into a uterus. A visualization element is within or on a distal steerable portion of the sheath. The visualization element is capable of determining a location of a fibroid on wall of the uterus while the sheath is in the uterus. Typically, the visualization element comprise an ultrasonic transducer. For example, the visualization element may comprise a phased array transducer having 64 elements or a mechanically scanned transducer. Still further, the element may comprise other visualization means, such as hysteroscopy, that is capable of producing a visual image. At least one self-anchoring treatment needle is within or on a distal portion of the sheath. The treatment needle is deployable against the fibroid whose position has been located by the visualization element.

The at least one treatment needle, usually two treatment needles, will be anchored by providing a geometry which inhibits displacement after the needles have been deployed. Exemplary geometries include non-linear, such as arcuate, helical, such as cork screw, curved, co-axial, everting, and like configurations. For example, the geometry may comprises a pair of converging or diverging needles which when deployed in tissue will remain firmly anchored as a result of the opposed geometry. Such geometries may be conveniently referred to as being "self-anchoring." Such anchoring needles advantageously provide targeted treatment of larger volumes (e.g., larger fibroids) with less damage to non-target tissue. The treatment needle may take on a variety of forms, typically having both extended and retracted configurations, and be made from a variety of materials (e.g., nitinol). For example, the treatment needle may comprise electrodes, electrosurgical needles, or other tissue-penetrating elements capable of delivering ablative radiofrequency energy to target and treat the tumors. Alternatively, the treatment needle may comprise an antenna capable of delivering microwave energy to treat the fibroid. Further, the treatment needle may comprise a hollow tube so as to deliver at least one therapeutic agent to the fibroid. Still further, the treatment needle may comprise a cutting tube so as to morcelate the fibroid.

The visualization element will preferably be located near and/or coupled to the treatment needle so that needle positioning, deployment, and treatment is within a surgeon's field of view. The sheath, visualization element, and/or treatment needle may be integrally formed or comprises separate, modular components that are coupleable to one another. For example, the visualization element may comprise a re-usable ultrasound core that may be positioned within a disposable needle carrying sheath. Further, at least a portion of the sheath, visualization element, and/or treatment needle may be steerable, rotatable, deflectable, flexible, pre-shaped, or pre-formed so as provide transvaginal access to the uterus for identification and treatment of fibroids. An exemplary interventional deployment and imaging system is described in more detail in co-pending U.S. Provisional Patent Application Ser. No. 60/758,881, filed Jan. 12, 2006, which is assigned to the assignee of the present application and incorporated herein by reference.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIG. 8 illustrates an eighth embodiment of the method and device comprising laproscopically injecting bubbles containing drugs that are activated by intra-uteral ultrasound imaging.

FIG. 10 illustrates a method of laproscopically imaging and treating a fibroid.

FIGS. 11A through 11C illustrate methods of decoupling the ultrasound imaging from the steerable, flexible needle catheter.

DETAILED DESCRIPTION OF THE INVENTION

Figure 1E:
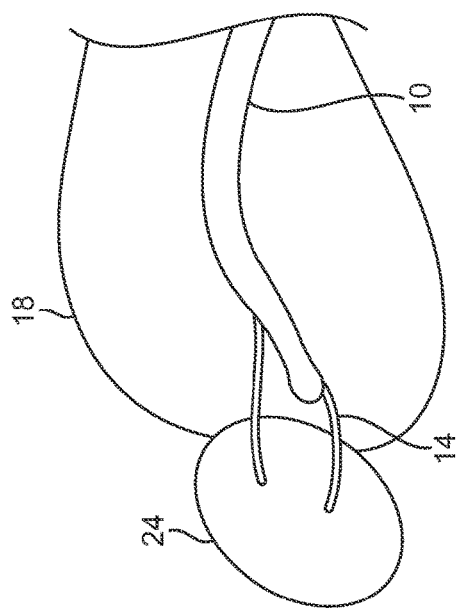
FIGS. 1A though 1F illustrate a first embodiment of the method and device comprising converging ablation needles and on board ultrasound imaging constructed in accordance with the principles of the present invention.
Figure 1F:
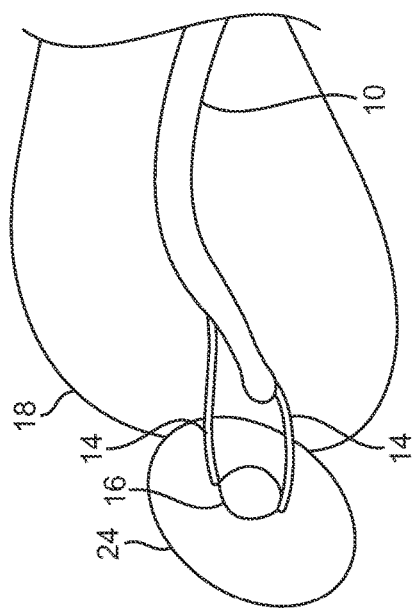
Figure 1D:
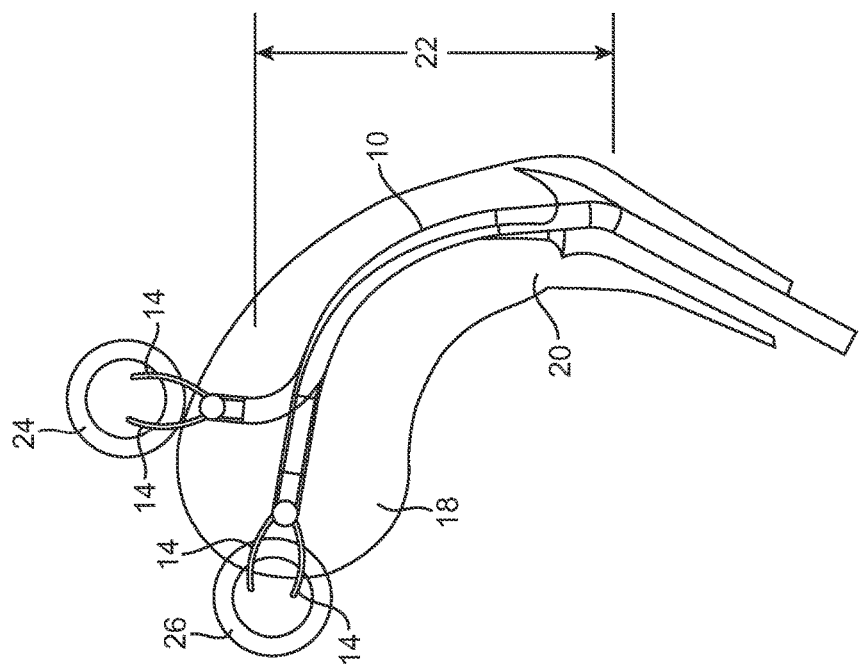

Referring now to FIGS. 1A through 1F, a first embodiment of the invention is illustrated including two converging ablation needles 14 and an ultrasound imaging module 12. A flexible, steerable catheter 10 is shown that acts as a sheath for the ultrasound catheter 12. In FIG. 1A, the two treatment needles 14 are in a retracted configuration within the sheath 10. In FIG. 1B, the ultrasound catheter 12 is shown within the sheath 10 with the two treatment needles 14 in a deployed configuration. One or both converging ablation needles 14 may have insulating sleeves so as to prevent treating non-target tissue and/or thermocouples at a tip region to measure a tissue temperature. FIG. 1C shows application of radiofrequency ablation energy between the two bipolar needle electrodes 14 and the resulting energy field 16 therebetween. FIG. 1D shows the sheath 10 inserted into the uterus 18 via the cervix 20 with a flexible shaft portion 22. As described above, the ultrasound beam 12 not only allows for identification of the fibroids 24, 26, but also serves to provide real-time visualization of needle anchoring and ablation treatment. The ultrasound catheter 12 may further be steered, rotated, or deflected independently of the treatment needles 14 so as to allow for a complete reconstruction view. For example, the ultrasound catheter may be torqued or rotated so that positioning of both needles 14 and treatment 16 may be verified. FIG. 1E show deployment of the treatment needles 14 during ultrasound visualization while FIG. 1F shows radiofrequency ablation treatment 16 of the fibroid tumor 24. Generally, each individual fibroid tumor 24, 26 will be navigated to, imaged, targeted and treated separately. It will be appreciated that the above depictions are for illustrative purposes only and do not necessarily reflect the actual shape, size, or dimensions of the device. This applies to all depictions hereinafter.

Figure 2A:
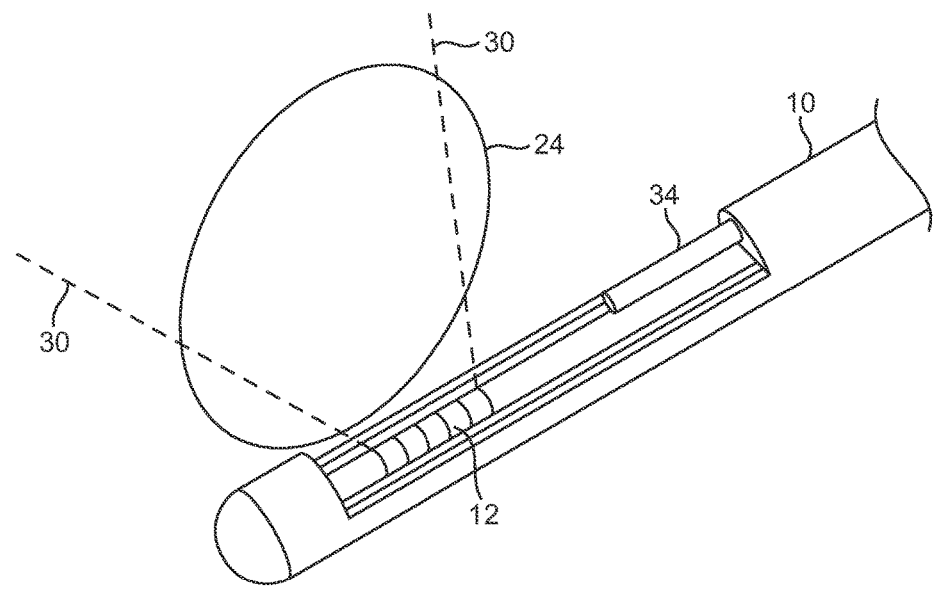
FIGS. 2A through 2D illustrate a second embodiment of the method and device comprising diverging ablation needles and on board ultrasound imaging constructed in accordance with the principles of the present invention.
Figure 2B:
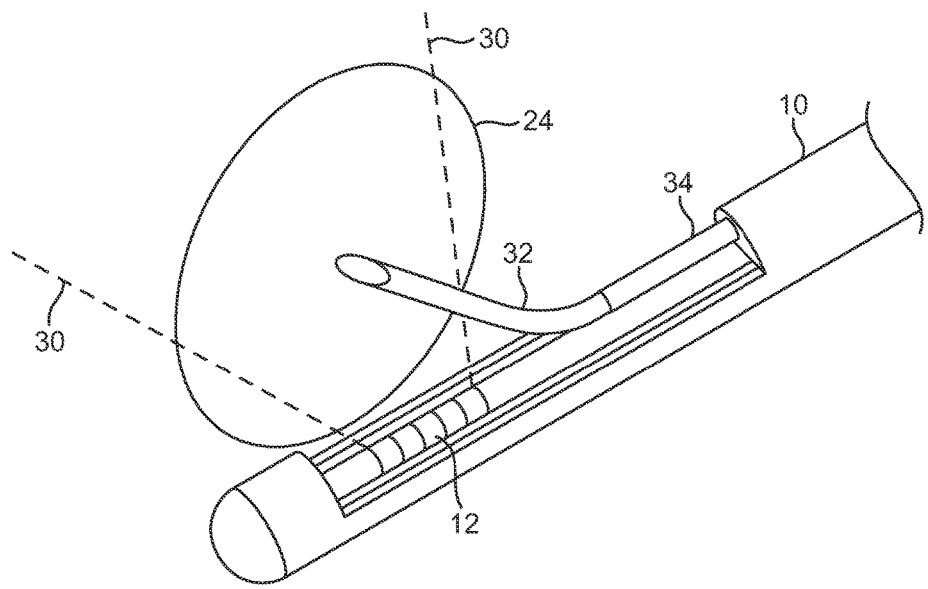
Figure 2C:
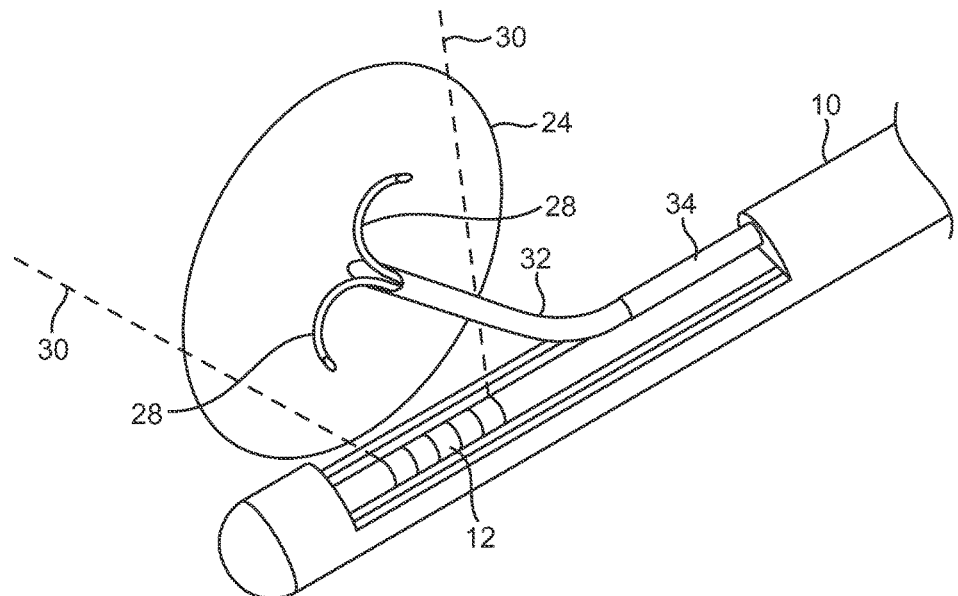
Figure 2D:
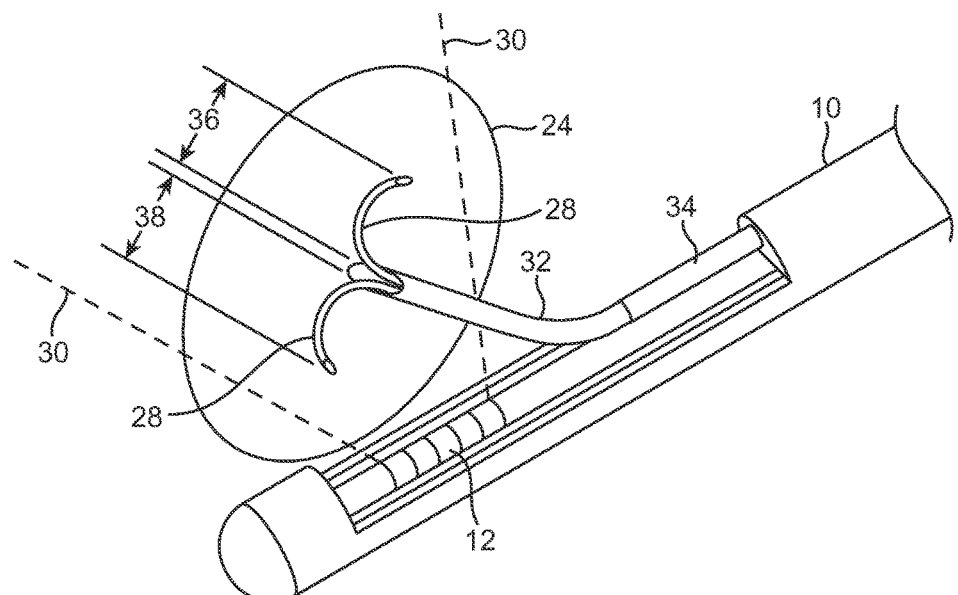

Referring now to FIGS. 2A through 2D, a second embodiment of the invention is illustrated including two diverging ablation needles 28 and the ultrasound imaging module 12. Again, the flexible, steerable catheter 10 is shown acting as a sheath for the ultrasound catheter 12. In FIG. 2A, the ultrasound catheter 12 is inserted into the sheath 10 and is visualizing the fibroid tumor 24 within the uterus in an imaging field transverse to an axis of the sheath as denoted by the dashed lines 30. A hollow nitinol needle 32 is deployed through a lumen 34 in the sheath 10 and across the imaging field, as illustrated in FIG. 2B. Thereafter, two hooked treatment needles 28 are deployed through the hollow needle 32 within the limits of the imaging field as illustrated in FIG. 2C and anchored against the fibroid 24. Radiofrequency ablative energy is then delivered in a bipolar fashion between the two poles of the hooked treatment needles 28 while the treatment needles remain with the limits of the imaging field so as to necrose the fibroid tissue 24 as illustrated in FIG. 2D. Fibroid identification, needle deployment, and ablation treatment are carried out under ultrasound visualization 30 in real-time. It will be appreciated that the distances (as denoted by arrows 36, 38) that each treatment needle 28 is deployed within the fibroid tissue 24 may be adjusted based on the size of the lesion.

Figure 3A:
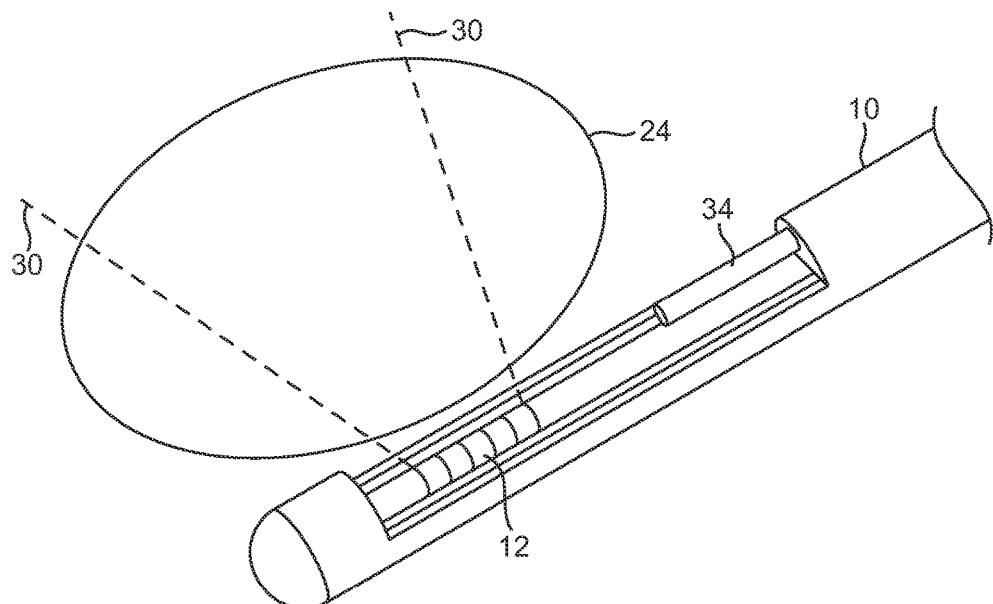
FIGS. 3A through 3D illustrate a third embodiment of the method and device comprising telescoping ablation needles and on board ultrasound imaging constructed in accordance with the principles of the present invention.
Figure 3B:
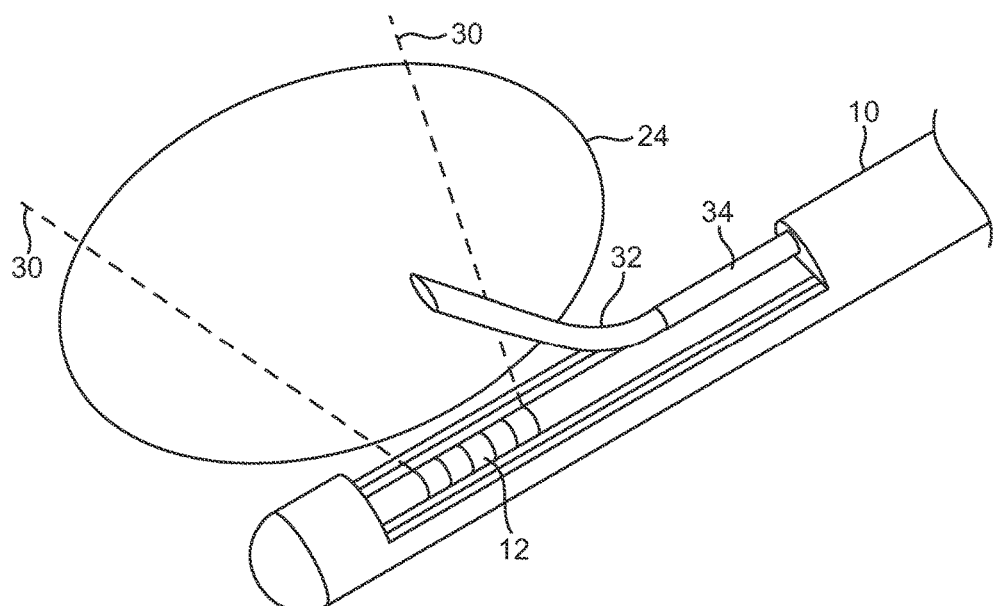
Figure 3C:
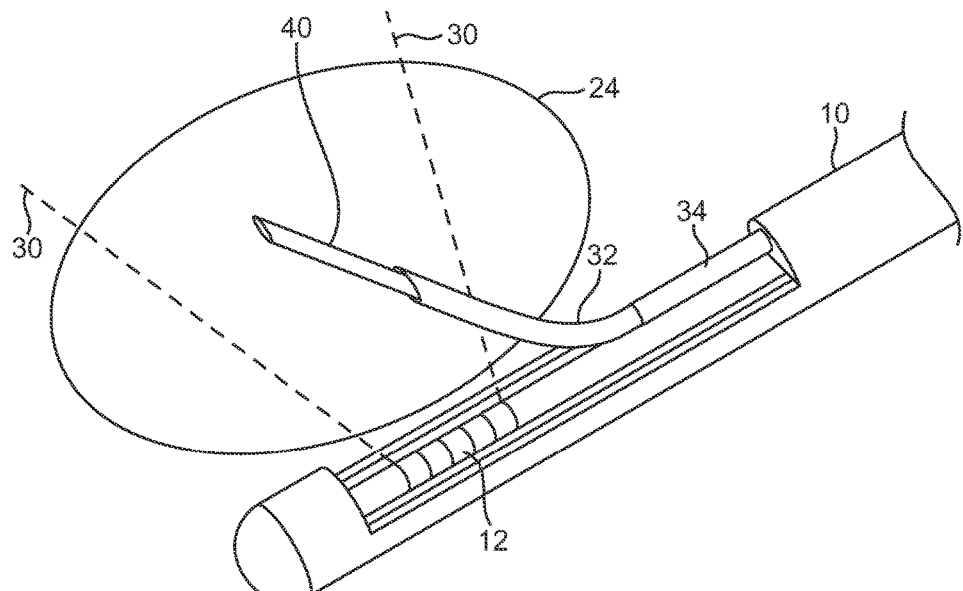
Figure 3D:
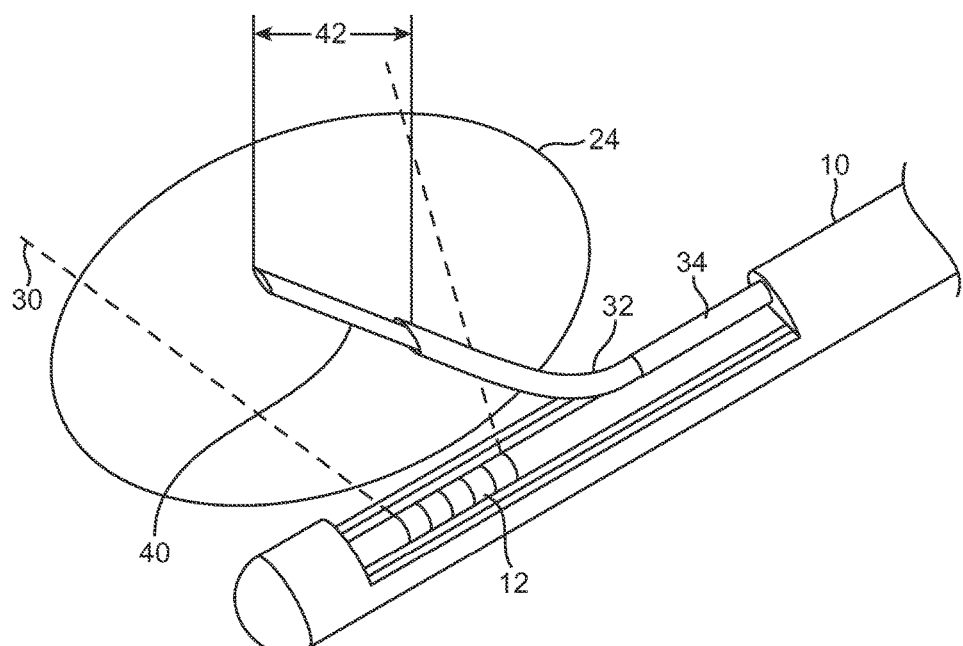

Referring now to FIGS. 3A through 3D, a third embodiment of the invention is illustrated including a telescoping ablation needle 40 and the ultrasound imaging module 12. Again, the flexible, steerable catheter 10 is shown acting as a sheath for the ultrasound catheter 12. As shown in FIG. 3A, the ultrasound catheter 12 is inserted into the sheath 10. The sheath 10 is transcervically introduced into the uterus and used for visualizing the fibroid tumor 24 as denoted by the dashed lines 30. Similar to FIG. 2B, a first nitinol needle 32 is deployed through the lumen 34 in the sheath 10. Thereafter, a second telescoping needle 40 is deployed through the first needle 32 as illustrated in FIG. 3C. Radiofrequency ablative energy is delivered in a bipolar fashion between the two telescoping needles 40, 32 under ultrasound visualization 30. Again, the distance (as denoted by arrow 42) that the telescoping treatment needle 40 is extended within the fibroid tissue 24 may be adjustable to the size of the lesion.

Figure 4A:
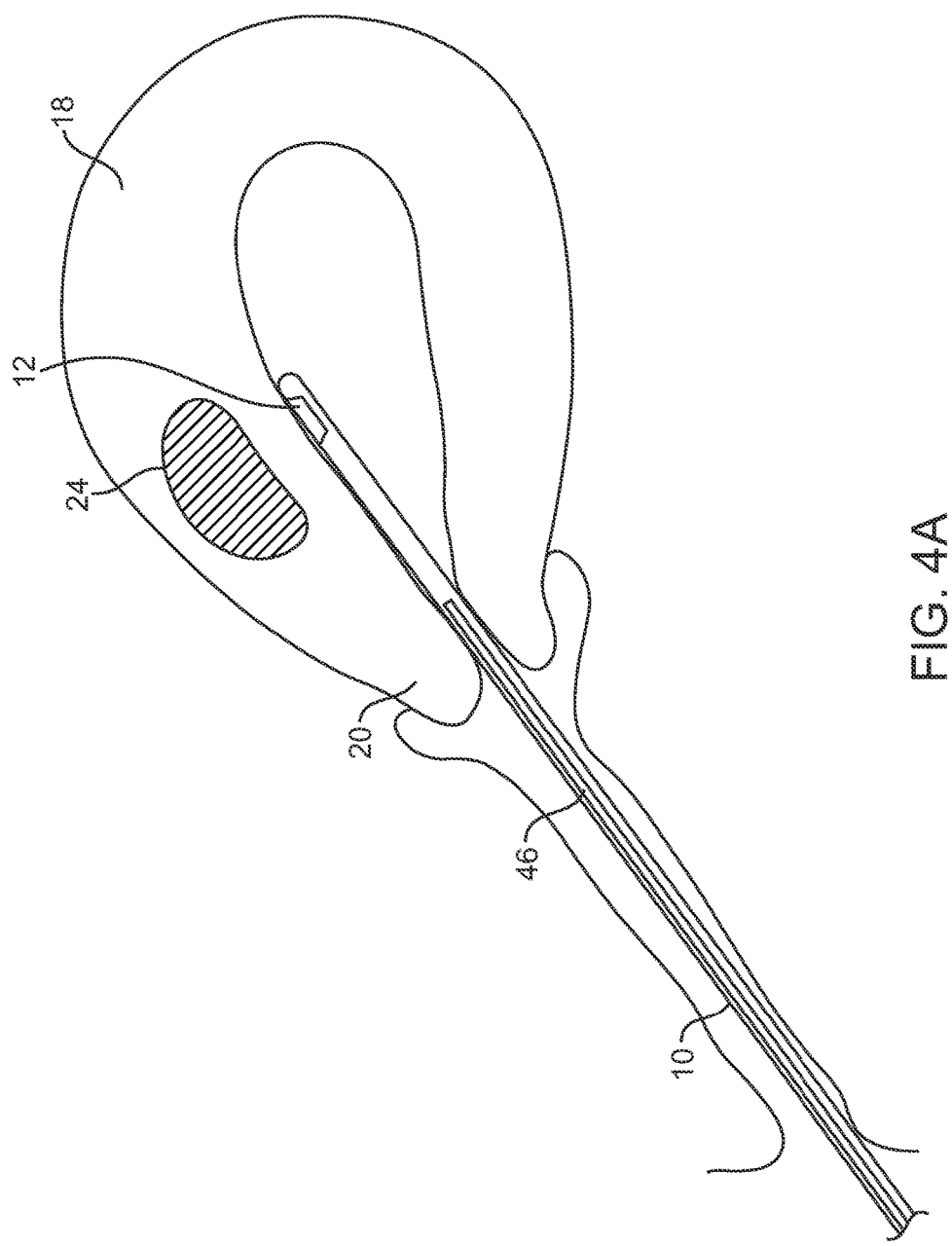
FIGS. 4A through 4F illustrate a fourth embodiment of the method and device comprising an inflatable balloon which provides treatment and on board ultrasound imaging constructed in accordance with the principles of the present invention.
Figure 4B:
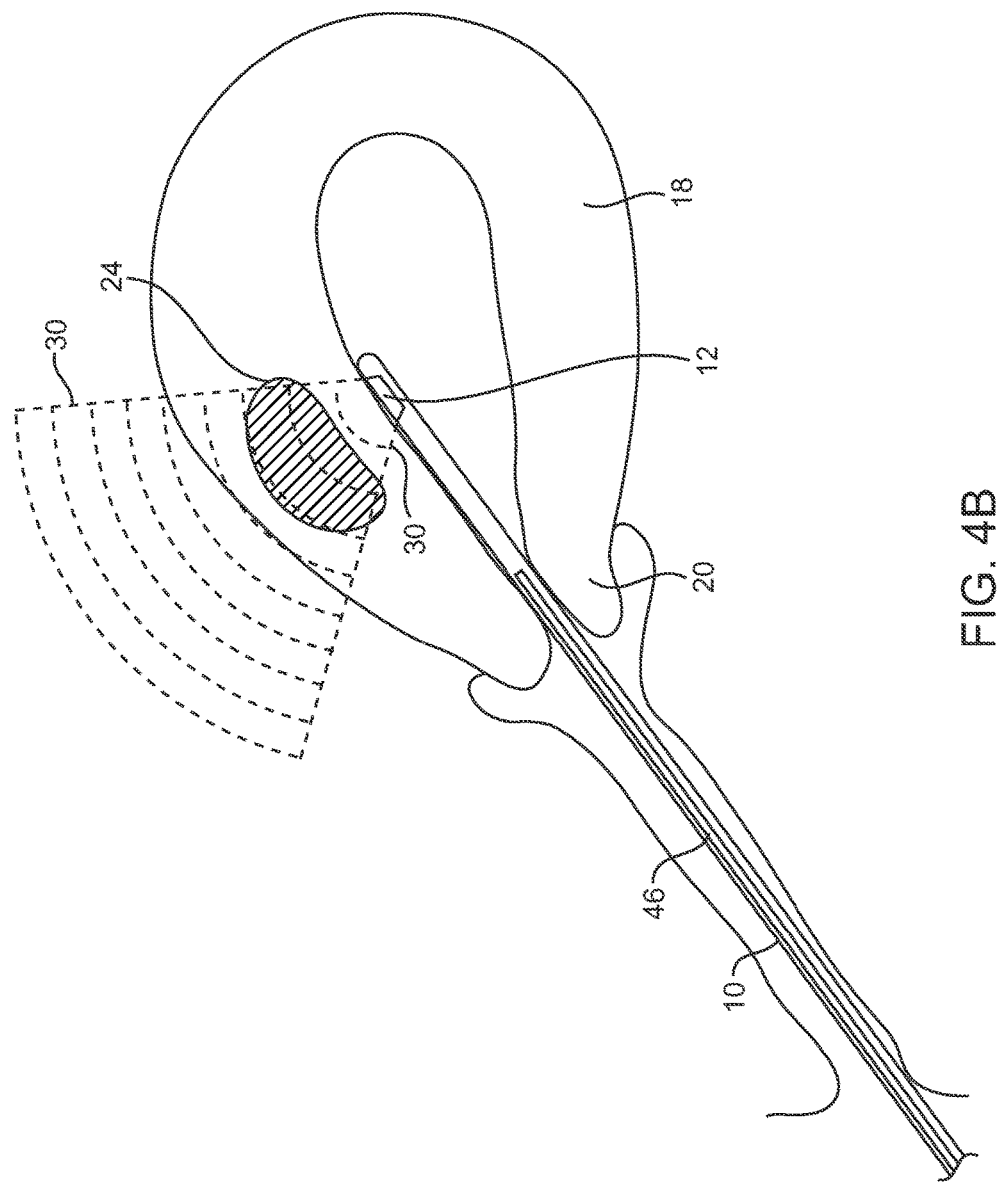
Figure 4C:
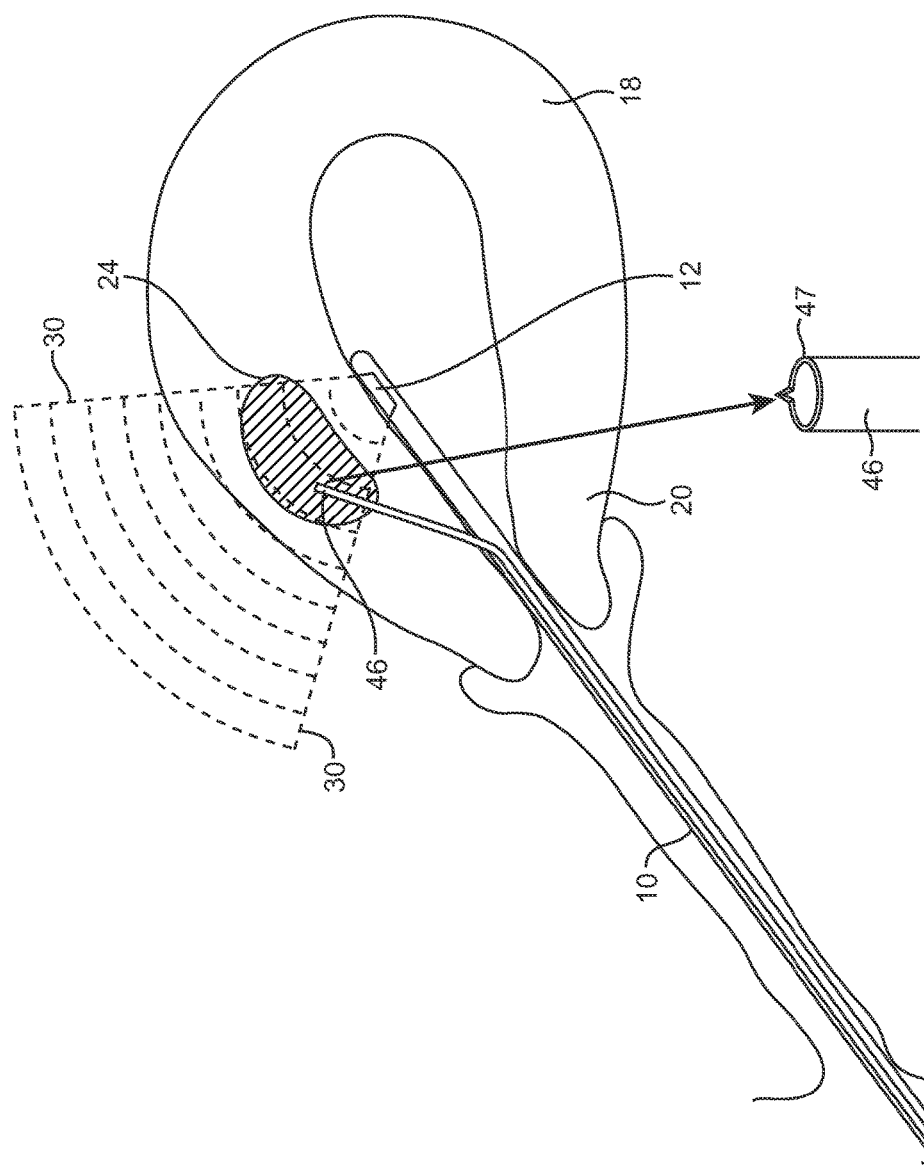
Figure 4D:
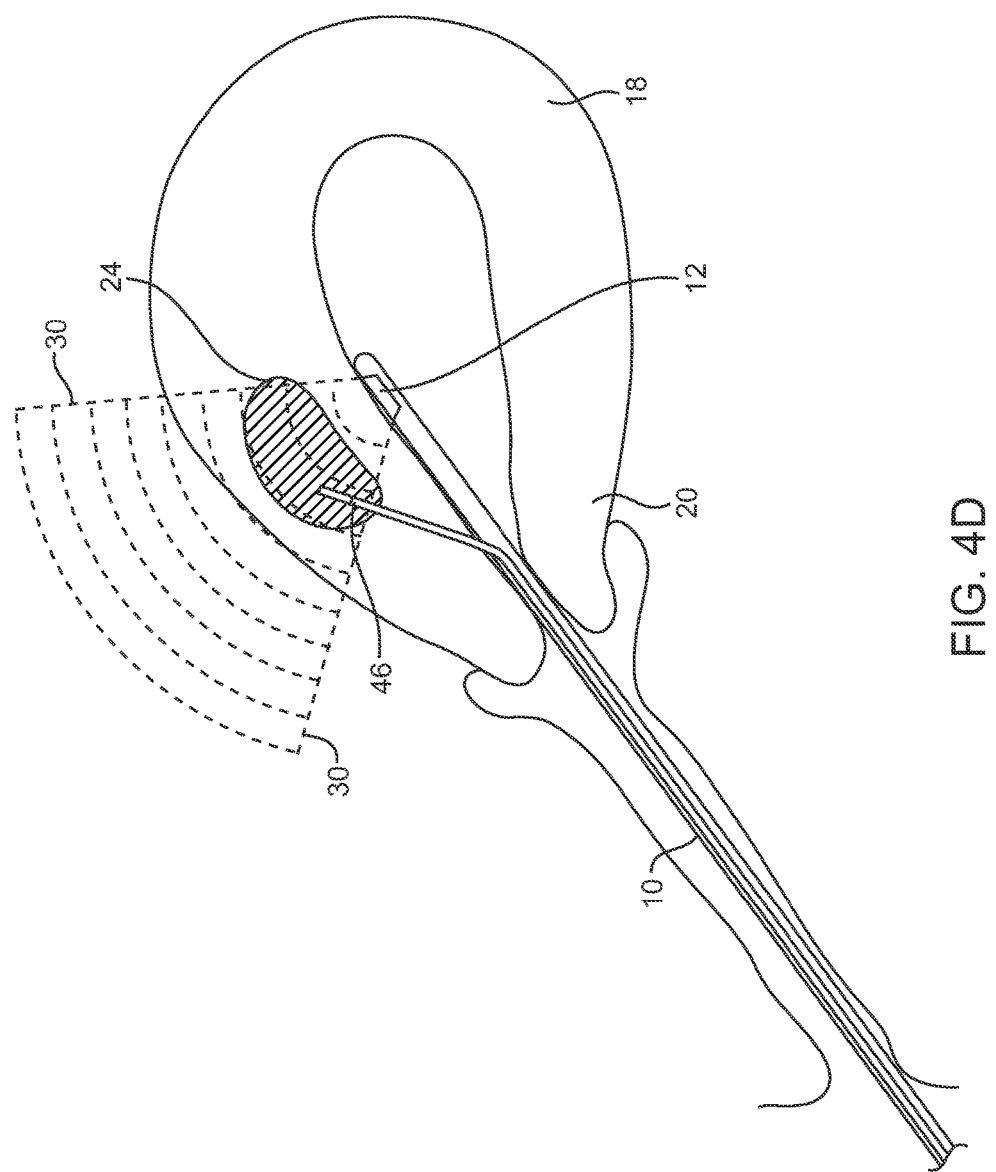
Figure 4E:
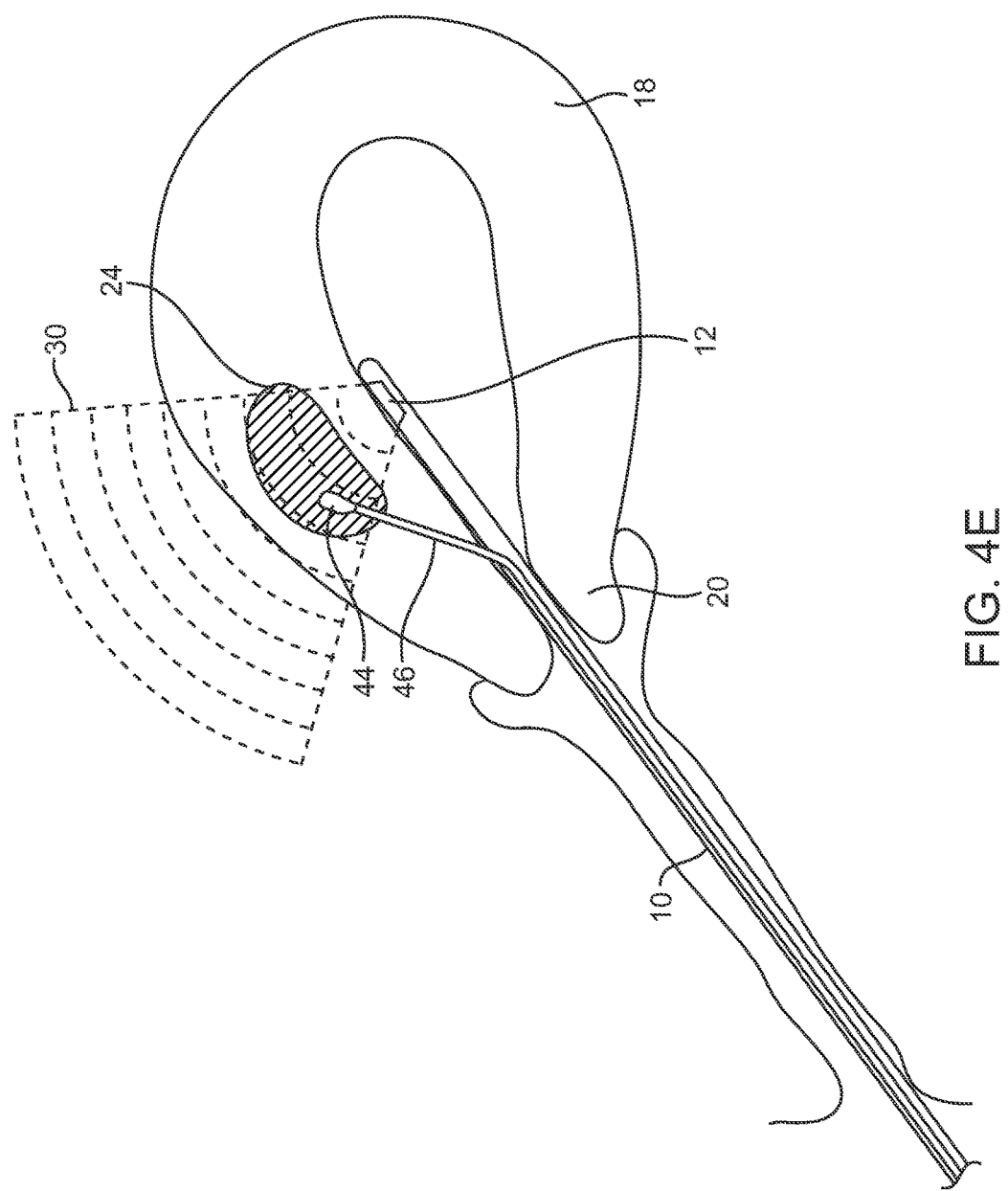
Figure 4F:
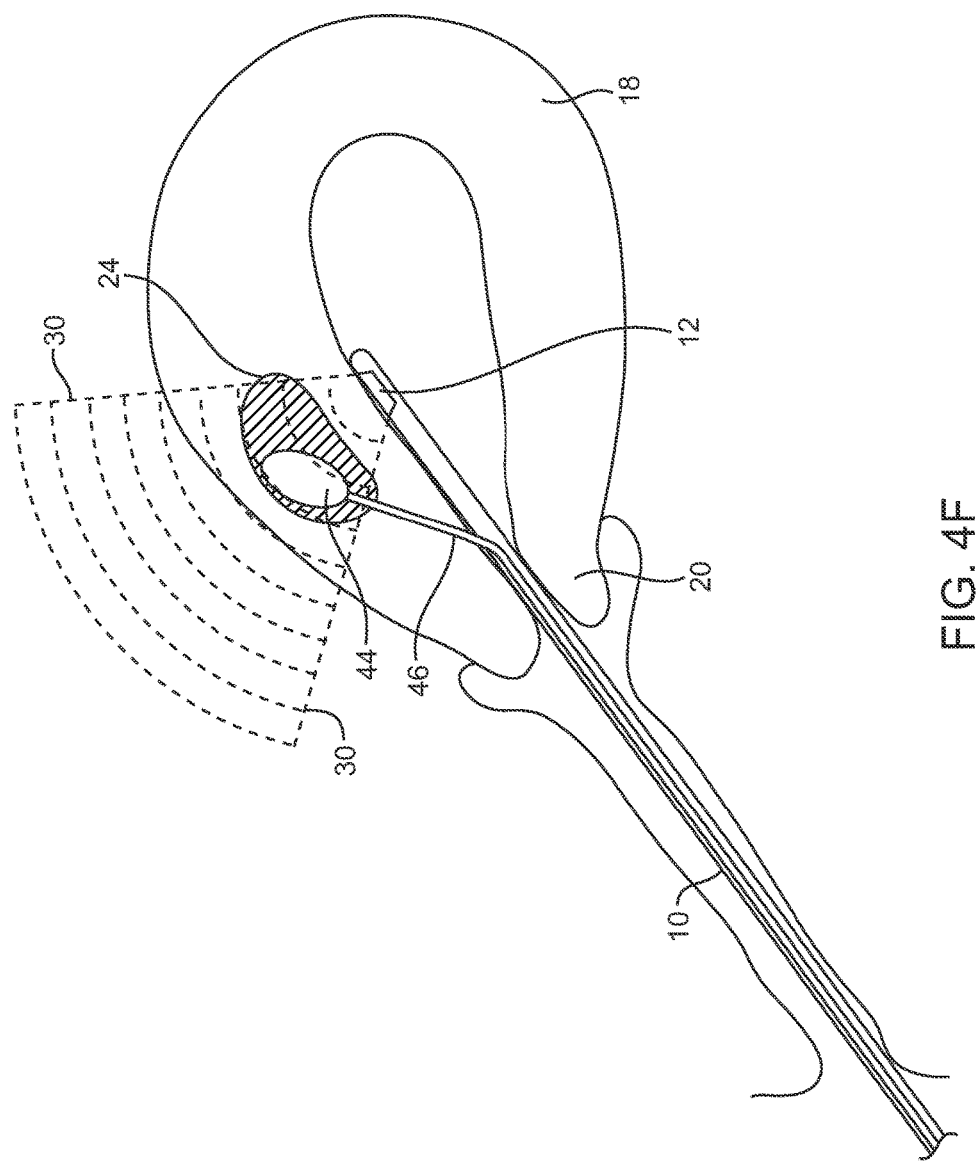

Referring now to FIGS. 4A through 4F, a fourth embodiment of the invention is illustrated including an inflatable treatment balloon 44 and the ultrasound imaging catheter 12. As shown in FIG. 4A, the flexible, steerable sheath 10 is inserted into the uterus 18 via the cervix 20 with the ultrasound module 12 on board. The sheath 10 further has a lumen for insertion of a rotary cutting tube 46, treatment needle, or other penetrating device. FIG. 4B illustrates visualization of the individual fibroid tumor 24 from within the uterine cavity 18 by the ultrasound module 12, as denoted by the dashed lines 30. FIG. 4C illustrates advancement and penetration of the rotary cutting tube 46 into the fibroid tumor 24 under direct visualization 30 through the ultrasound module 12. The distal end of the rotary cutting tube 46 is depicted with a morcelating tip 47. In FIG. 4D, some of the fibroid tissue 24 is removed through the rotary cutting tube 46 to create room for the treatment balloon 44. The rotary cutting tube 46 is further partially retracted to make room in the tumor 24 for the treatment balloon 44. As shown in FIG. 4E, the treatment balloon 44 is then deployed through the cutting tube 46 and into the tumor 24 under direct visualization 30 through the ultrasound module 12. As shown in FIG. 4F, the treatment balloon 44 is inflated and ablative energy is applied by the balloon 44 to treat the tumor 24 under direct visualization 30 through the ultrasound module 12. The ablative energy may comprise any of the energy sources described herein including radiofrequency energy, microwave energy, laser energy, cryo energy, ultrasound energy, HIFU, or radiation. Alternatively or in addition to the treatment balloon 44, a radiofrequency basket electrode may be disposed over the balloon to treat the tumor.

Figure 5A:
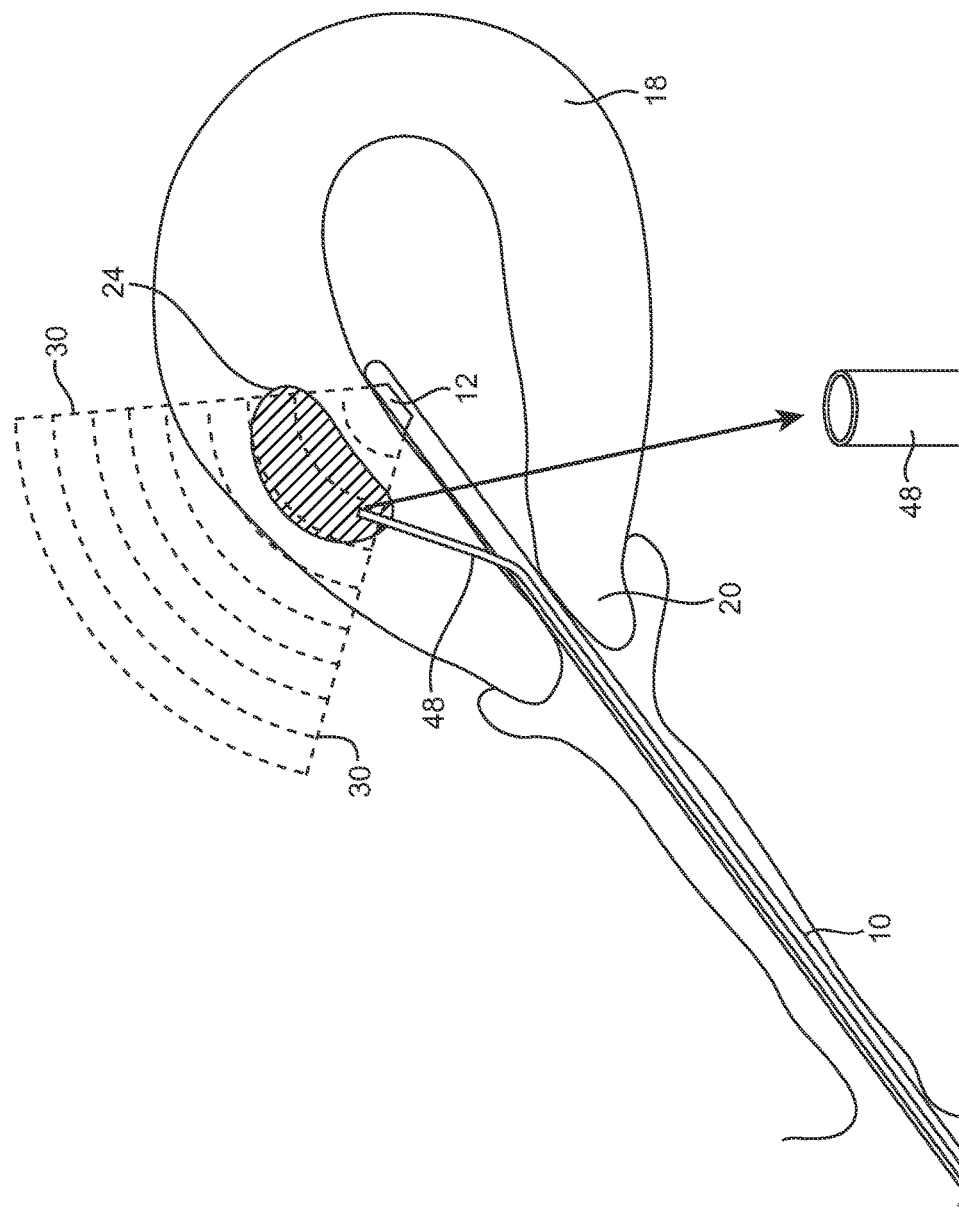
FIGS. 5A through 5C illustrate a fifth embodiment of the method and device comprising another inflatable balloon which provides treatment and on board ultrasound imaging constructed in accordance with the principles of the present invention.
Figure 5B:
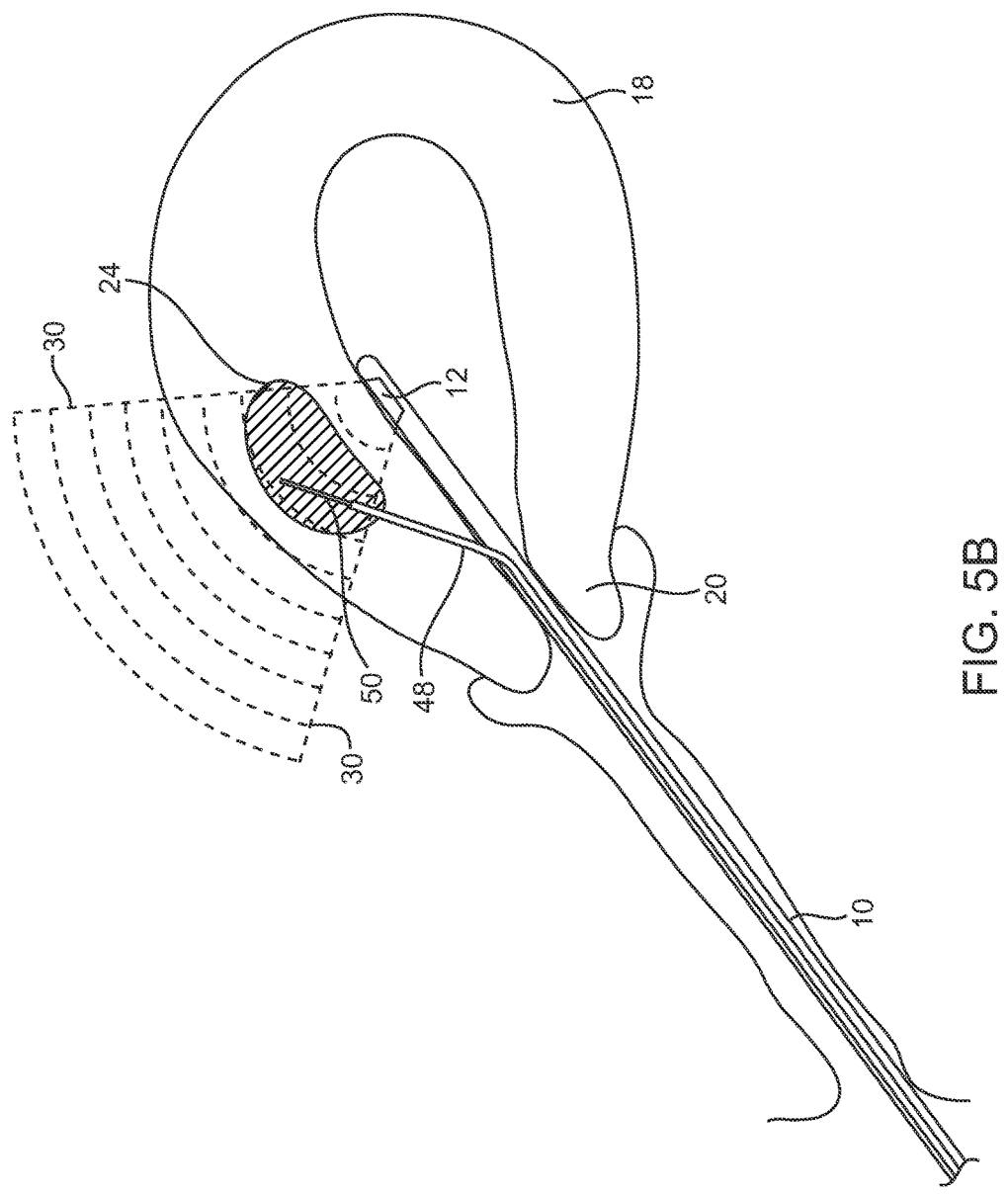
Figure 5C:
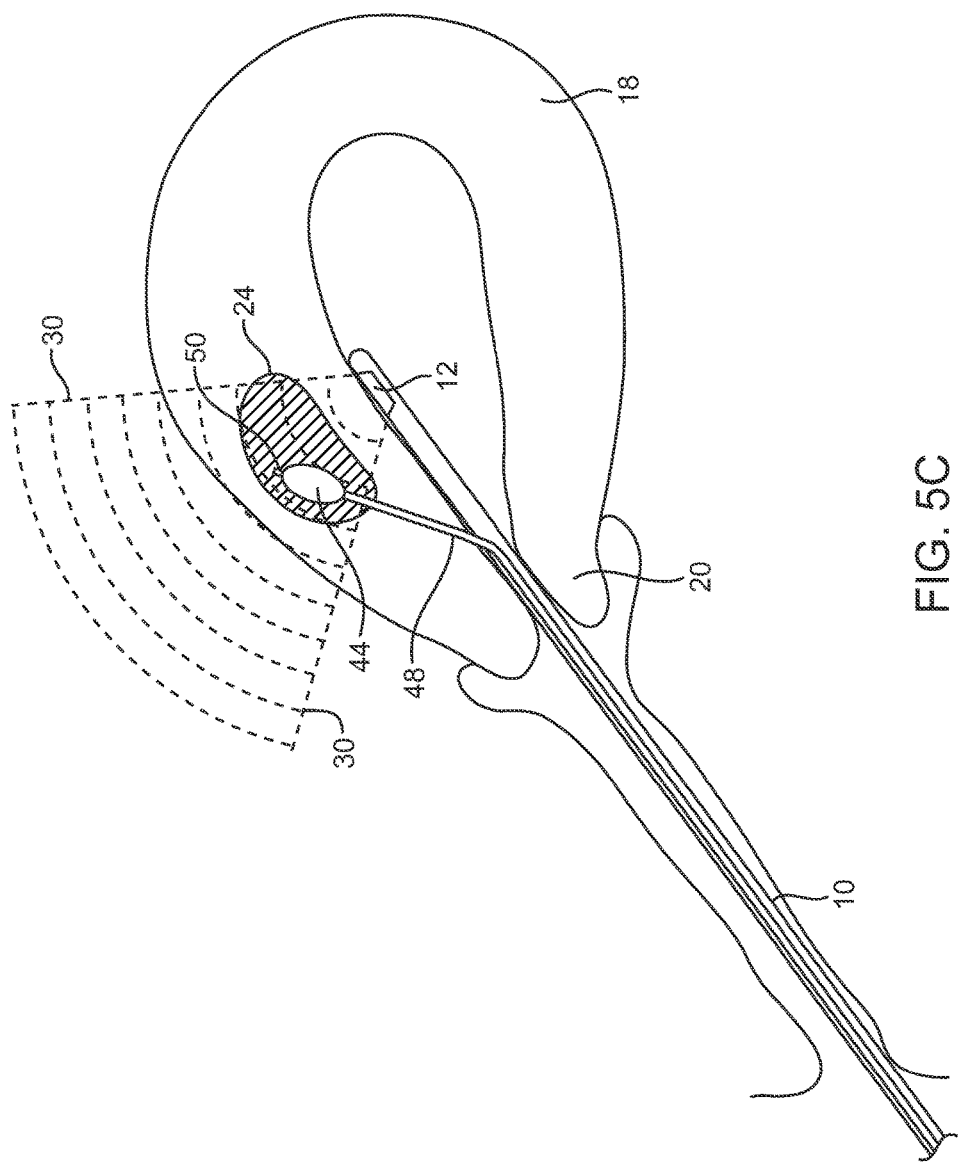

Referring now to FIGS. 5A through 5C, a fifth embodiment of the invention is illustrated including the inflatable treatment balloon 44 and the ultrasound imaging catheter 12 of FIG. 4F. This embodiment differs in how the treatment balloon 44 is deployed into the tumor 24. After identification of the fibroid tumor 24 from within the uterine cavity 18, a rotary cutting tube 48 without a morcelating tip is advanced and penetrated into the fibroid tumor 24 under direct visualization 30 through the ultrasound module 12 as shown in FIG. 5A. A wire 50 is then advanced into the tumor 24 through the cutting tube 48 under direct visualization 30 through the ultrasound module 12 in FIG. 5B. In FIG. 5C, the treatment balloon 44 is advanced through the cutting tube 48 and over the wire 50 and then inflated in the tumor 24 under direct ultrasound visualization 30 so as to treat the tumor 24 with ablative energy. The ablative energy may comprise any of the energy sources described herein including radiofrequency energy, microwave energy, laser energy, cryo energy, ultrasound energy, HIFU, or radiation.

Figure 6:
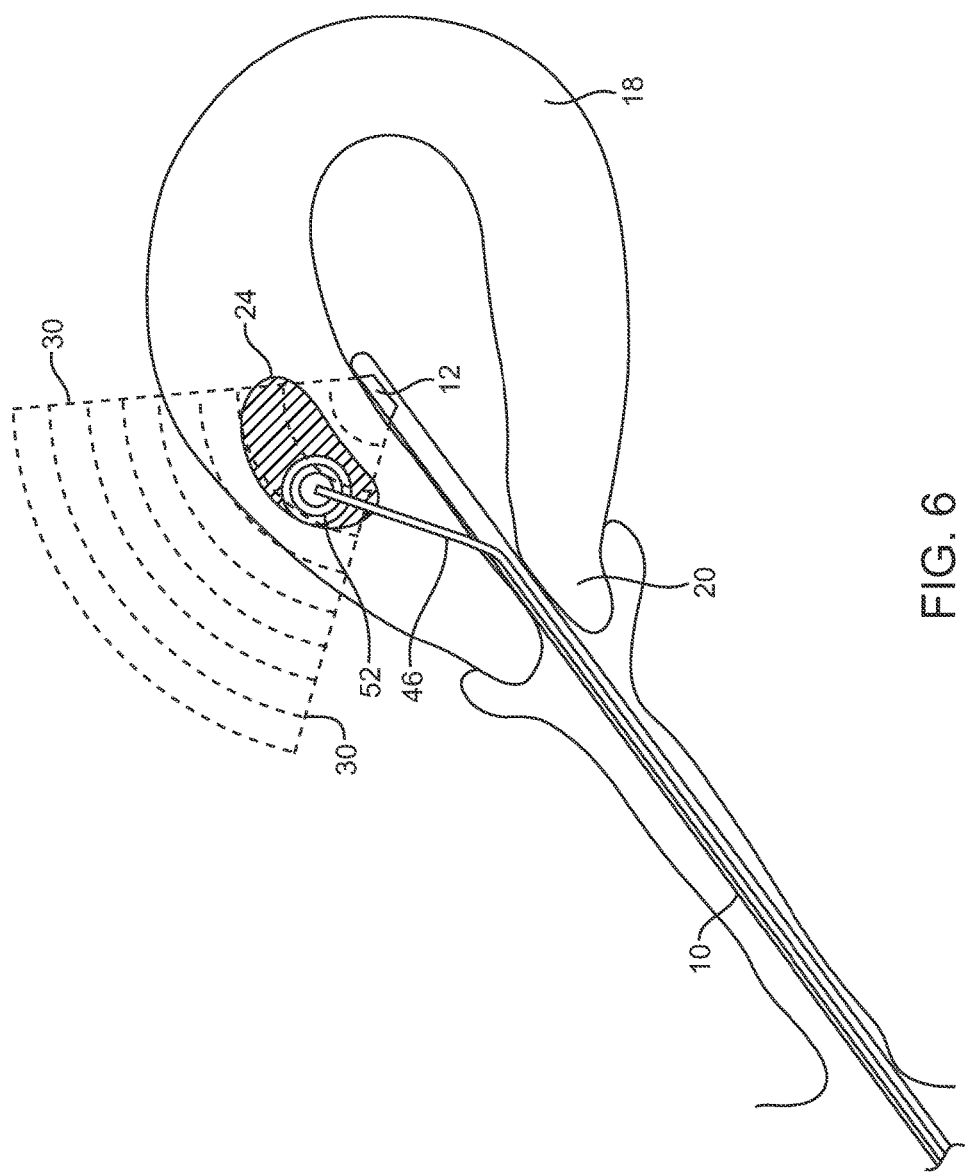
FIG. 6 illustrates a sixth embodiment of the method and device comprising a mechanical cutting element having a morcelating tip and on board ultrasound imaging constructed in accordance with the principles of the present invention.

Referring now to FIG. 6, a sixth embodiment of the invention is illustrated including the rotary cutting tube 46 and the ultrasound imaging catheter 12 of FIG. 4C. This embodiment differs in that the rotary cutting tube 46 itself provides treatment of the tumor 24 with its mechanical cutting element having a morcelating tip 47. After identification of the fibroid tumor 24 and advancement/penetration of the rotary cutting tube 46 into the fibroid tumor 24 under direct visualization 30 through the ultrasound module 12 in the uterus 18, the fibroid 24 is morcelated or liquefied by the rotary cutting tube 46 and the fibroid tissue 24 is suctioned out through the hollow cutting tube 46 as depicted by reference numeral 52.

Figure 7B:
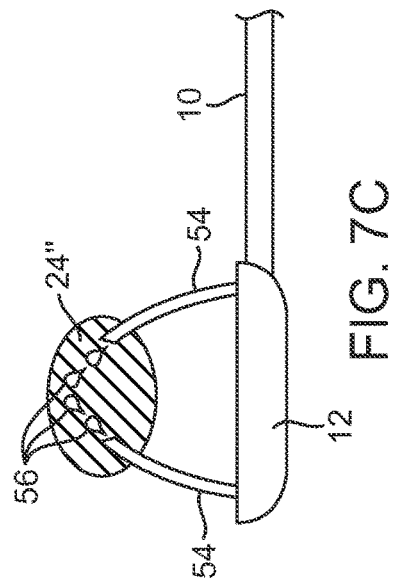
FIGS. 7A through 7C illustrate a seventh embodiment of the method and device comprising drug delivery needles and on board ultrasound imaging constructed in accordance with the principles of the present invention.
Figure 7C:
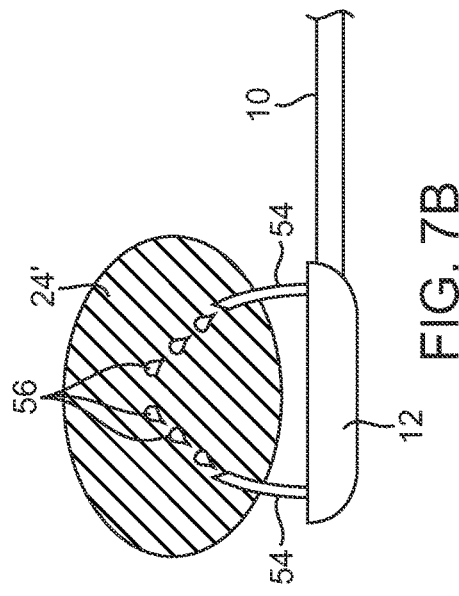
Figure 7A:
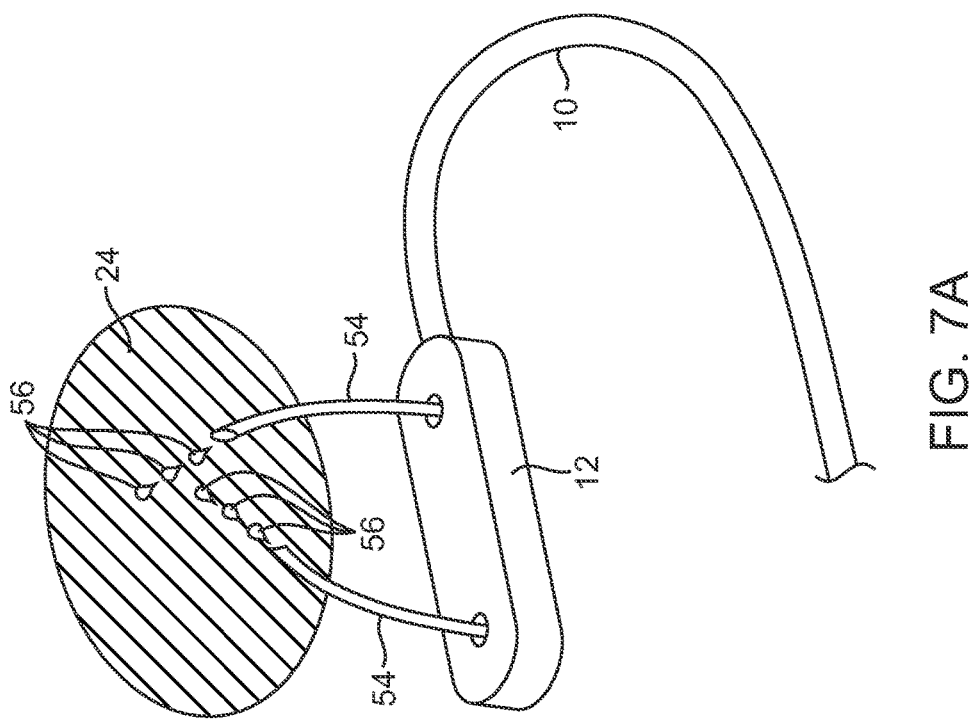

Referring now to FIGS. 7A through 7C, a seventh embodiment of the invention is illustrated including a drug delivery needle 54 and the ultrasound imaging catheter 12. In FIG. 7A, under ultrasound visualization in the uterus, two treatment needles 54 are anchored within the fibroid 24 and the fibroid treated by the delivery of at least one therapeutic agent 56 to the fibroid with the needles 54. It will be appreciated that the treatment needles 54 may have both a retracted and extended position and may be adjustable so as to achieve the desired drug delivery profile. Further, drug delivery may take place though a single treatment needle 54 or through multiple treatment needles 54. The therapeutic agent 56 may comprise a variety of agents. For example, the agent 56 may comprise a chemotherapeutic or chemoablative agent (e.g., alcohol or a chemokine), a gene therapy agent, a tissue necrosis agent, an antibody, or the like. The drug delivery needles 54 may treat tumors of various sizes. For example, FIG. 7B illustrates treatment of a large tumor 24' (e.g., 40 mm), while FIG. 7C illustrates treatment of a smaller tumor 24" (e.g., 20 mm).

Referring now to FIG. 8, another drug delivery method and device is illustrated. A syringe 58 is used to laproscopically inject contrast bubbles 60 containing at least one therapeutic agent 56 into the fibroid 24 instead of transcervical drug delivery via treatment needles 54. After drug delivery injection into the fibroid 24, the ultrasound imaging catheter 12 in the uterus 18 activates the agent 56 by targeted ultrasound 30. For example, this may cause the bubbles 60 to burst or break in the fibroid blood supply 24 which in turn releases the therapeutic agent 56 to the fibroid 24 for treatment.

Figure 9A:
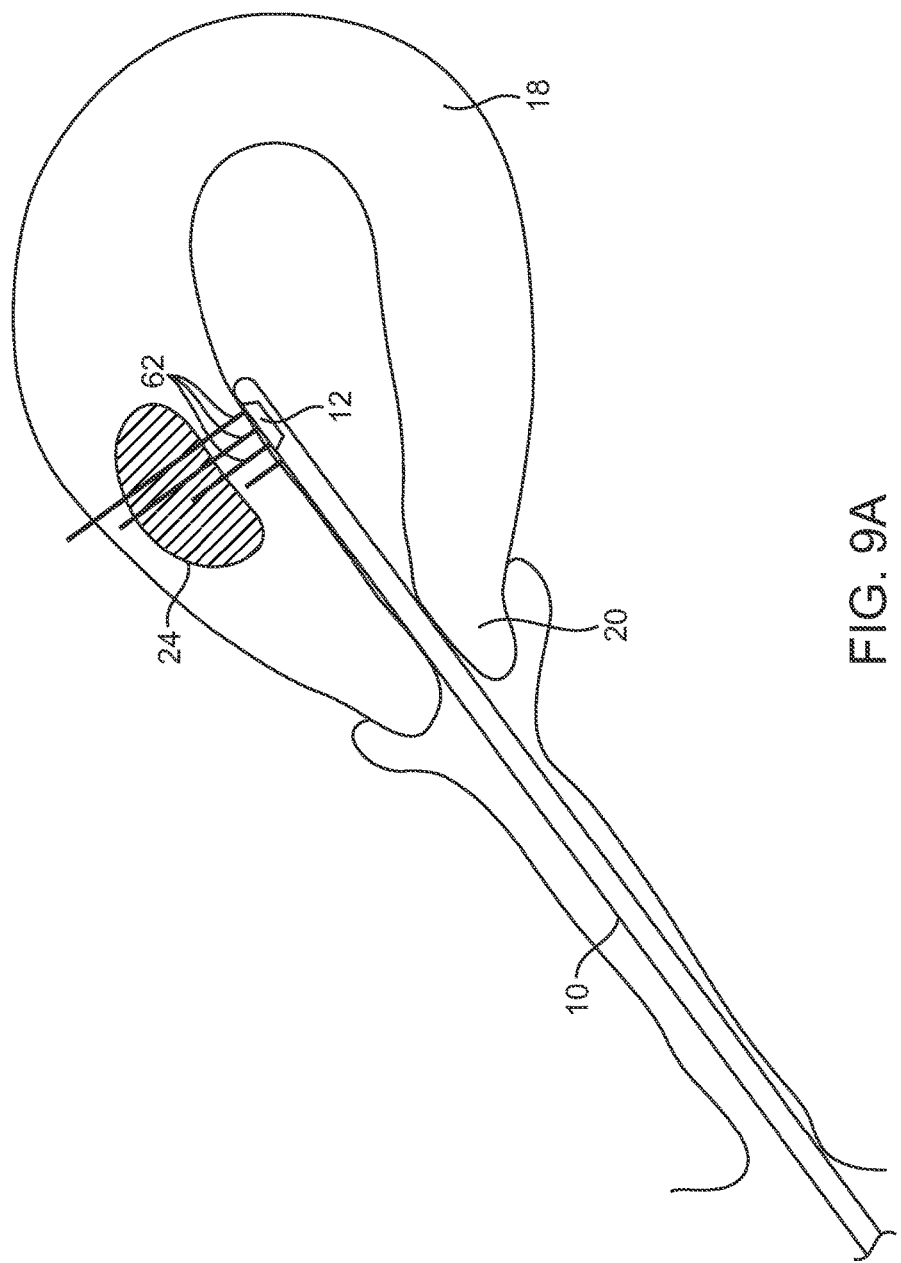
FIGS. 9A and 9B illustrate impedance monitoring for directed fibroid treatment which may be employed with the present invention.

Referring now to FIG. 9A, the flexible, steerable catheter 10 is shown inserted into the uterus 18 via the cervix 20. The catheter 10 has an on board ultrasound imaging module 12 and a lumen for insertion of at least one needle 62 or other penetrating device. In this illustration, multiple needles 62 are shown inserted into the fibroid tumor 24 with impedance monitoring to denote the change in the impedance of the tissue from inside the tumor 24 versus tissue outside the tumor 24 and/or tissue outside the uterine wall. Impedance monitoring will aid in directly targeting the fibroid tumor 24 for treatment (e.g., energy delivery, drug delivery, mechanical cutting, etc.) and may also safely control treatment delivery so that it is only within the uterus 18 itself. Further, impedance profiling may denote border recognition of tissue. This in turn may allow for implementation of additional safety mechanisms. For example, automatic shutoff of the device may be implemented if the needle 62 is extended beyond the fibroid 24 and/or uterus 18.

Figure 9B:
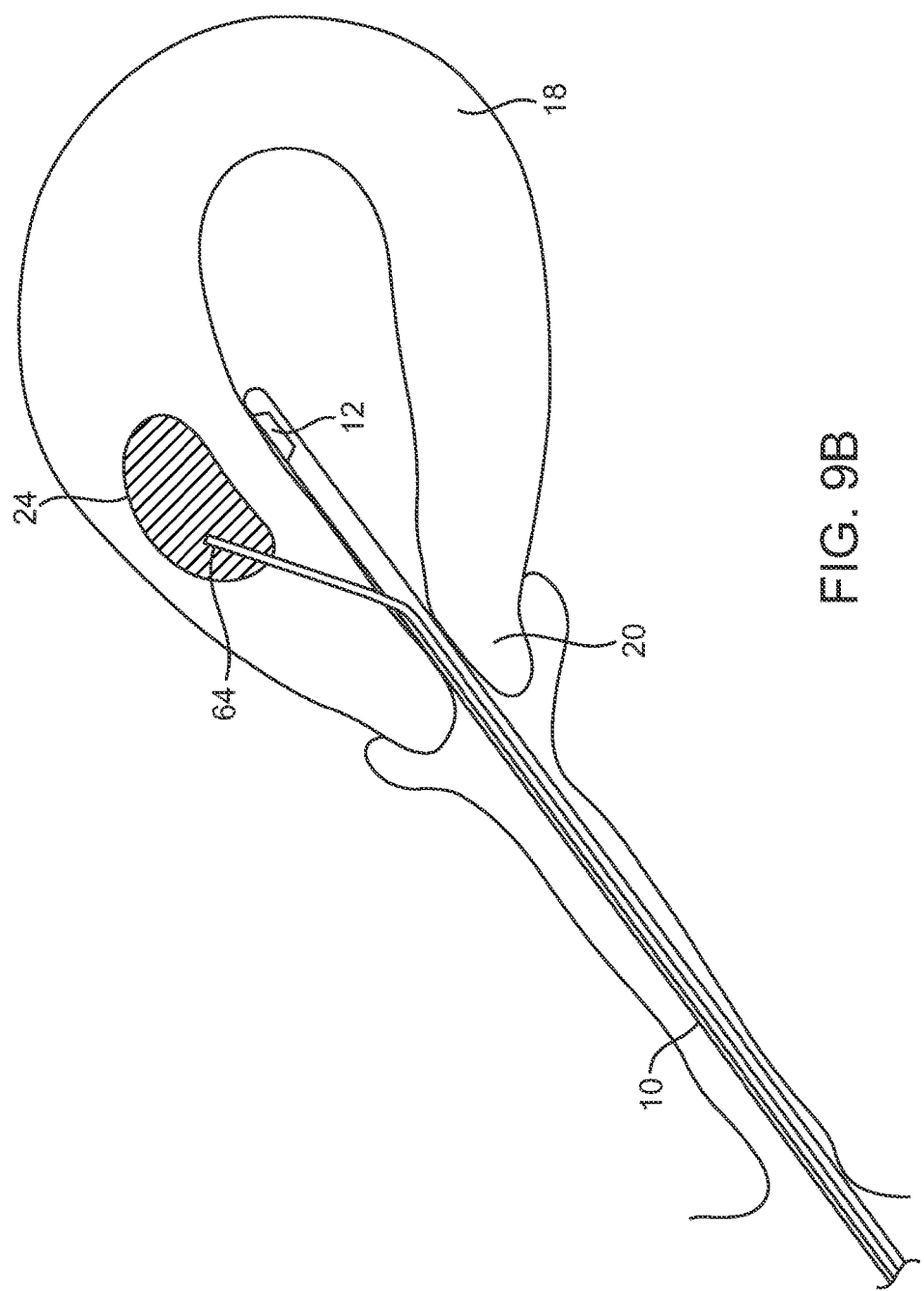

Referring now to FIG. 9B, the flexible, steerable catheter 10 is shown inserted uterus 18 via the cervix 20. The catheter 10 has an on board ultrasound imaging module 12 and a lumen for insertion of at least one needle 64 or other penetrating device. The needle 64 is shown inserted into the fibroid tumor 24 with impedance monitoring to denote the change in the impedance of the tissue from inside the tumor 24 versus tissue outside the tumor and/or tissue outside the uterine wall. Impedance monitoring will aid in directly targeting the fibroid tumor 24 for treatment from the uterine wall.

Referring now to FIG. 10, a flexible, steerable laparoscopic probe 10 is shown accessing the uterus 18 from an abdominal port 66 in the abdominal wall 68. The probe 10 uses the ultrasound module 12 outside of the uterus 18 to target fibroid tumors 24 that are within the uterus 18. The probe 10 then uses the treatment needle 70 under direct visualization 30 through the ultrasound module 12 to then treat the fibroid 24 with ablative energy.

Figure 11B:
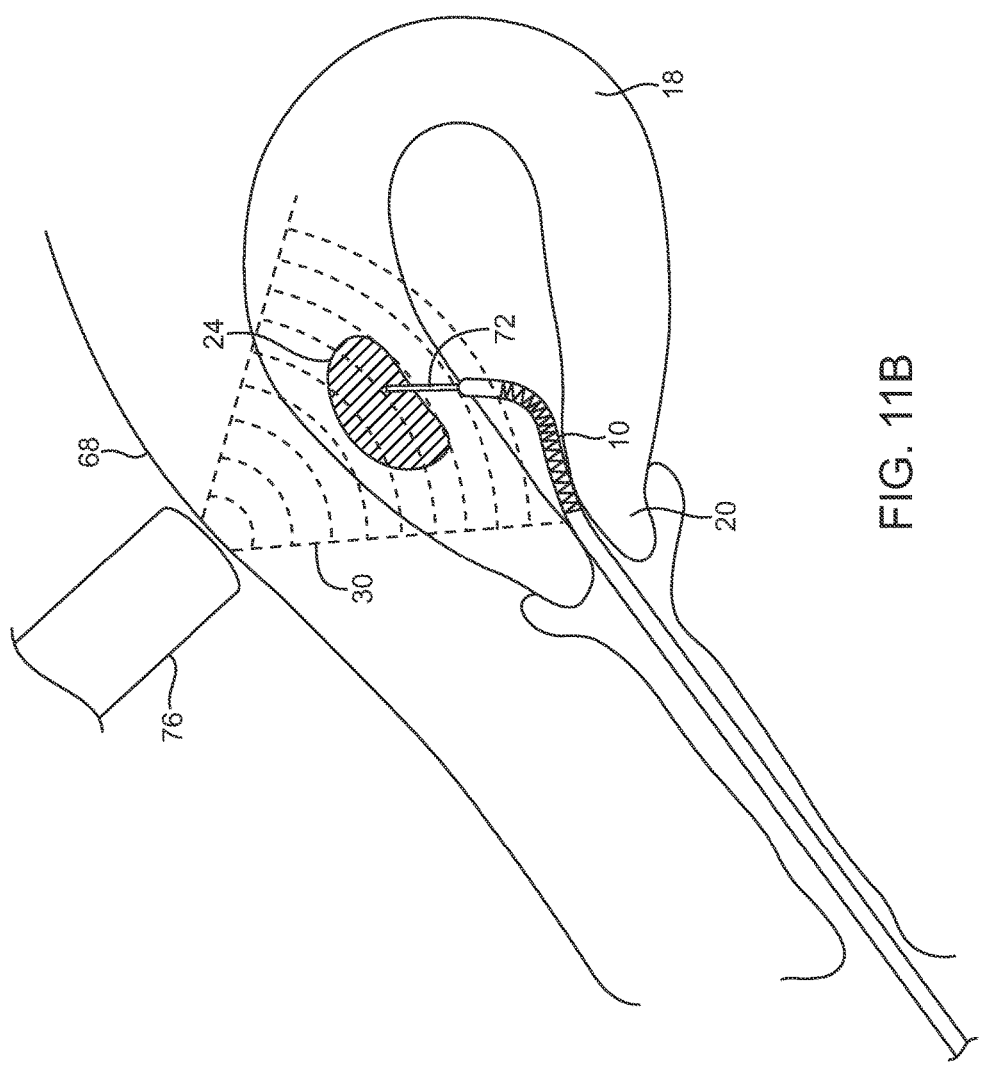

Referring now to FIG. 11A, a flexible, steerable catheter based probe 10 having a treatment needle 72 is shown inserted into the uterus 18 and within the fibroid 24 using a non-coupled vaginal ultrasound probe 74. The two devices 10, 74 are operated independently of each other. Referring now to FIG. 11B, the flexible, steerable needle catheter 10 is shown inserted into the uterus 18 and the treatment needle 72 within the fibroid 24 using a non-coupled abdominal ultrasound probe 76. The two devices 10, 76 are operated independently of each other. With respect to FIG. 11C, the flexible, steerable laparoscopic needle probe 10 is shown accessing the uterus 18 from an abdominal port 66 in the abdominal wall 68. The treatment needle 70 of the probe 10 is shown accessing the fibroid 24 with the aid of ultrasound visualization 30 from the abdominal ultrasound probe 76. The two devices 70, 76 are operated independently of each other.

Figure 12:
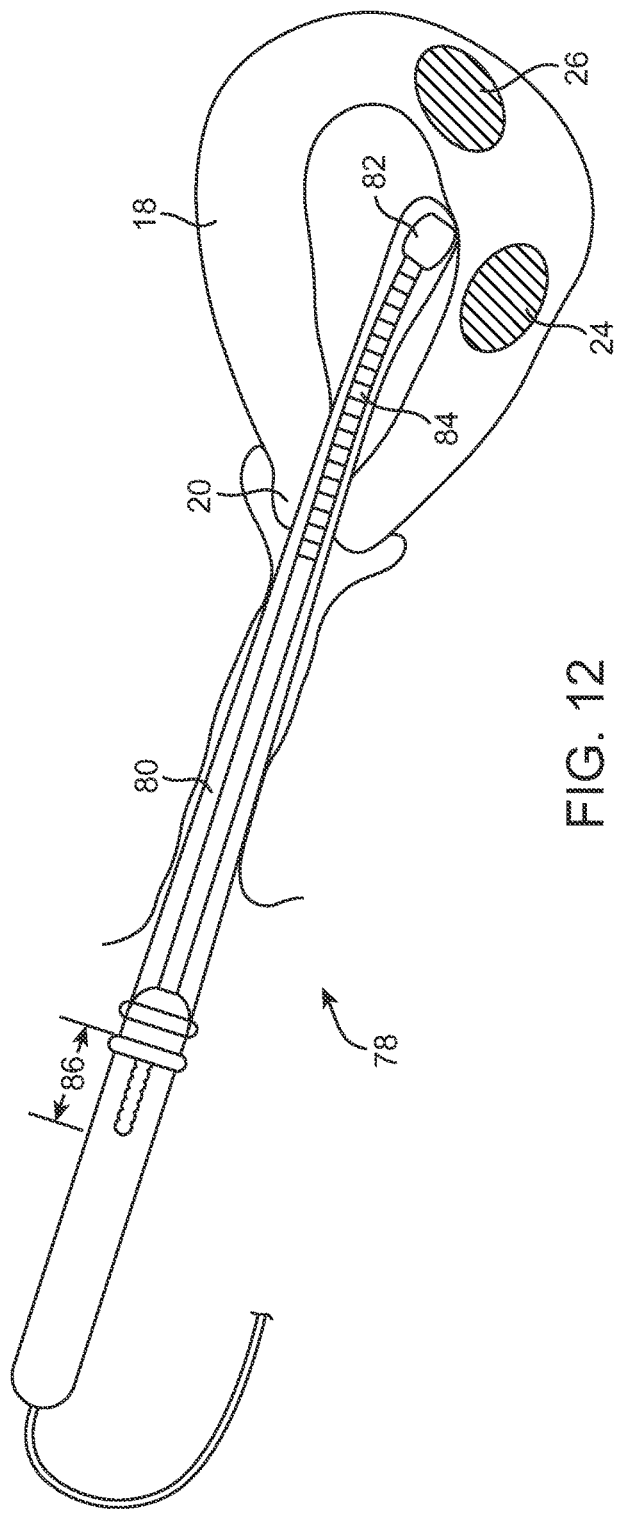
FIG. 12 illustrates a direct transuteral diagnostic ultrasound imager.

Referring now to FIG. 12, a flexible, steerable intrauterine ultrasound imaging device 78 is shown for imaging the uterine wall and lining transendometrially for the diagnosis of fibroids 24, 26. The ultrasound imaging head 82 generally comprises an ultrasonic phased array transducer having 64 elements. The ultrasound transducer may also be mechanical, linear, or curved. A sterile drape 80 may be placed over the diagnostic imager 78, wherein a gel may be used within the drape 80 for improved image coupling. The diagnostic imager 78 may also be used without a drape 80, when disposable, using natural body fluids for image coupling. The diagnostic imager 78 further has a flexible section 84 capable of deflection in a range from 0 degrees to about 90 degrees via an angle adjustment knob 86. The diagnostic ultrasound imager 78 is inserted directly into the uterine cavity 18, either with or without dilation of the cervix 20, in order to directly image the fibroids 24, 26 within the wall of the uterus 18. This imaging provides a closer and more direct view of the tumors 24, 46 in order to more accurately diagnose the location and characterization of the fibroids or other pathology.

Figure 13B:
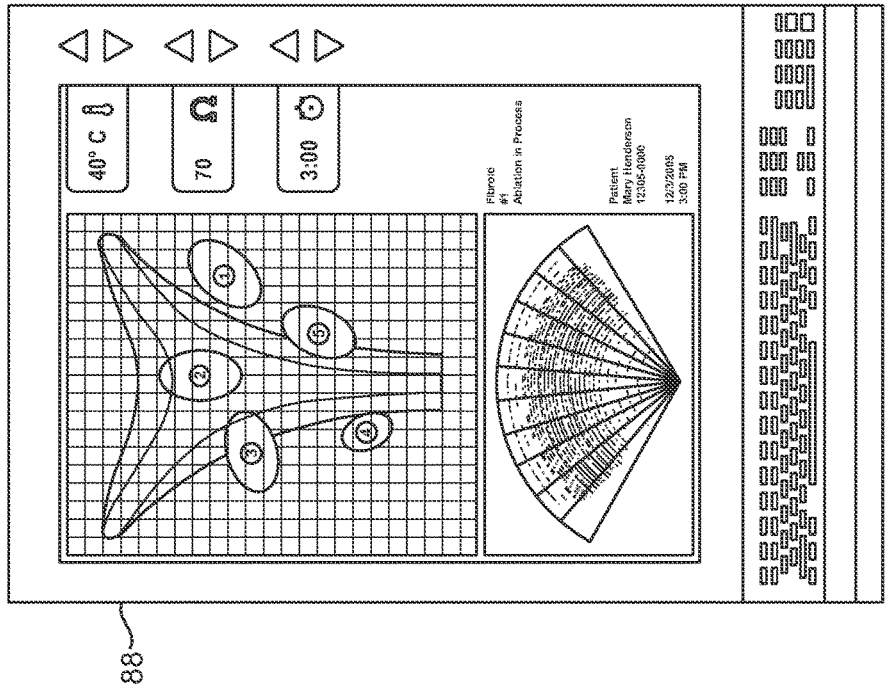
FIGS. 13A and 13B illustrate schematics of a system constructed in accordance with the principles of the present invention.
Figure 13A:
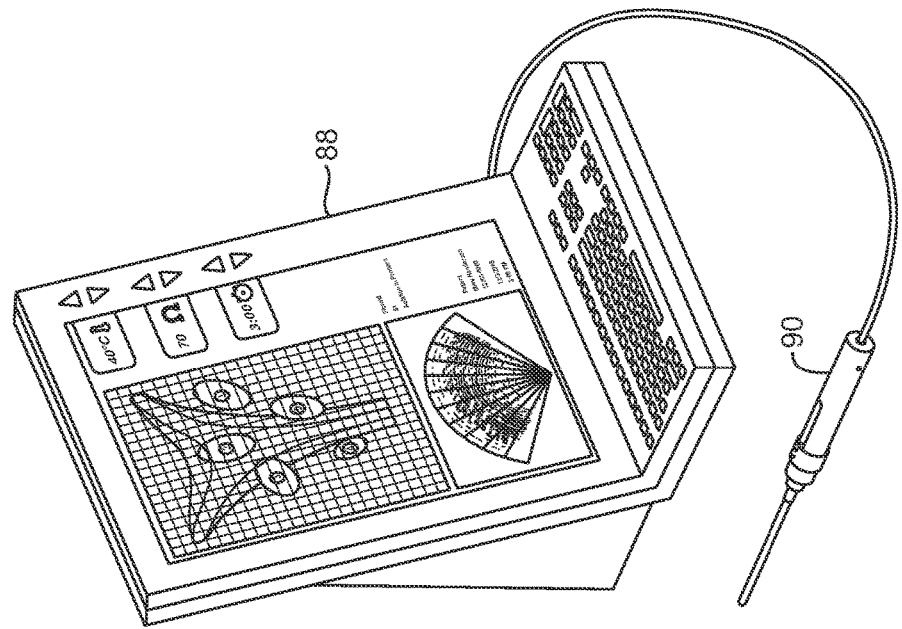

FIGS. 13A and 13B illustrate schematics of a system constructed in accordance with the principles of the present invention. The system comprises a combined ultrasound recognition and radiofrequency treatment system 88. The system 88 may provide a variety of features including ultrasound mapping, ultrasound recognition of treatment area (e.g., tissue differentiation via temperature profiling), radiofrequency ablation treatment under ultrasound imaging, temperature monitoring, time monitoring, and/or impedance monitoring. The system 88 may be coupled to various devices 90 described herein having single or multiple treatment needle configurations to ablate in either bipolar or monopolor modes.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method for minimally invasive treatment of uterine fibroids, said method comprising:
   introducing a sheath into a uterus, said sheath having a longitudinal axis;
   determining a location of a fibroid using a visualization element within or on the sheath, wherein the visualization element produces an imaging field transverse to the longitudinal axis of the sheath and wherein both the visualization element and the imaging field are deflectable with respect to the longitudinal axis of the sheath;
   advancing a hollow needle from the sheath through a wall of the uterus and across the imaging field;
   advancing a plurality of diverging needles from the hollow needle into the fibroid; and
   treating the fibroid with the diverging needles, wherein the diverging needles remain within the limits of the imaging field during treatment, and
   wherein determining the location of the fibroid comprises rotating the visualization element and the imaging field about the longitudinal axis of the sheath independently of the plurality of diverging needles after the hollow needle has been advanced through the wall of the uterus and across the imaging filed.

2. A method as in claim 1, wherein the sheath is introduced transcervically.

3. A method as in claim 1, wherein the visualization element is ultrasonic and produces a visual image.

4. A method as in claim 3, wherein introducing comprises manually positioning and penetrating the plurality of diverging needles through an endometrium so as to engage the fibroid.

5. A method as in claim 1, wherein treating the fibroid comprises delivering ablative energy to the fibroid with the plurality of diverging needles.

6. A method as in claim 5, wherein the ablative energy comprises radiofrequency energy, microwave energy, laser energy, cryo energy, ultrasound energy, HIFU, or radiation.

7. A method as in claim 6, wherein the ablative energy comprises radiofrequency energy delivered in a bipolar or monopolar fashion.

8. A method as in claim 1, wherein treating the fibroid comprises delivering at least one therapeutic agent to the fibroid with the plurality of diverging needles.

9. A method as in claim 1, further comprising imaging advancing the hollow needle, advancing the plurality of diverging needles, and treatment in real-time with the visualization element.

10. A method as in claim 1, further comprising monitoring tissue impedance.

11. A method as in claim 1, further comprising measuring a tissue temperature so as to aid in diagnosis, blood supply measurement, thermal signature, or tissue targeting.

* * * * *